US011209567B2

(12) United States Patent
McManamon et al.

(10) Patent No.: US 11,209,567 B2
(45) Date of Patent: Dec. 28, 2021

(54) SYSTEM, METHOD, AND FOR IMPROVING OILFIELD OPERATIONS

(71) Applicant: Exciting Technology, LLC, Dayton, OH (US)

(72) Inventors: Paul F. McManamon, Dayton, OH (US); J. Stephen Wills, Columbus, IN (US)

(73) Assignee: Exciting Technology, LLC, Dayton, OH (US)

( * ) Notice: Subject to any disclaimer, the term of this patent is extended or adjusted under 35 U.S.C. 154(b) by 280 days.

(21) Appl. No.: 16/068,171

(22) PCT Filed: Jan. 24, 2017

(86) PCT No.: PCT/US2017/014669
§ 371 (c)(1),
(2) Date: Jul. 5, 2018

(87) PCT Pub. No.: WO2017/127848
PCT Pub. Date: Jul. 27, 2017

(65) Prior Publication Data
US 2019/0018165 A1 Jan. 17, 2019

Related U.S. Application Data

(60) Provisional application No. 62/286,397, filed on Jan. 24, 2016.

(51) Int. Cl.
*G01V 3/30* (2006.01)
*G01V 3/16* (2006.01)
(Continued)

(52) U.S. Cl.
CPC .............. *G01V 3/30* (2013.01); *E21B 47/003* (2020.05); *E21B 47/11* (2020.05); *G01N 27/00* (2013.01);
(Continued)

(58) Field of Classification Search
CPC ... G01V 3/30; G01V 3/16; G01V 1/44; G01V 11/00; G01V 2200/16; G01V 2210/324; E21B 47/003; E21B 47/11; G01S 7/4802
See application file for complete search history.

(56) References Cited

U.S. PATENT DOCUMENTS 5,070,483 A * 12/1991 Berni ...................... G01S 17/50
367/14
7,405,834 B1 * 7/2008 Marron ................. G01S 7/4812
356/521

(Continued)

OTHER PUBLICATIONS

International Search Report corresponding to International application No. PCT/US2017/014669, dated Apr. 10, 2017, (17 pages).

*Primary Examiner* — Manuel L Barbee
(74) *Attorney, Agent, or Firm* — Maginot, Moore & Beck LLP

(57) ABSTRACT

A system includes a ground based area, an electromagnetic (EM) interrogation device having an EM emitter that directs an EM beam at the ground based area. The EM interrogation device includes a detector array that receives reflected EM radiation from the EM beam, and a controller having a ground movement description module that determines a movement profile of the ground based area in response to the reflected EM radiation.

40 Claims, 3 Drawing Sheets

(51) Int. Cl.
  *G01V 1/44*  (2006.01)
  *G01V 11/00*  (2006.01)
  *E21B 47/003*  (2012.01)
  *E21B 47/11*  (2012.01)
  *G01S 17/58*  (2006.01)
  *G01S 17/89*  (2020.01)
  *G01S 7/48*  (2006.01)
  *G01N 22/00*  (2006.01)
  *G01N 33/28*  (2006.01)
  *G01N 27/00*  (2006.01)

(52) U.S. Cl.
  CPC ............ *G01N 33/28* (2013.01); *G01S 7/4802* (2013.01); *G01S 17/58* (2013.01); *G01S 17/89* (2013.01); *G01V 1/44* (2013.01); *G01V 3/16* (2013.01); *G01V 11/00* (2013.01); *G01V 2200/16* (2013.01); *G01V 2210/324* (2013.01)

(56) References Cited

U.S. PATENT DOCUMENTS

| | | | |
|---|---|---|---|
| 7,728,295 | B2 | 6/2010 | Miles et al. |
| 8,633,699 | B2 | 1/2014 | Linscott et al. |
| 2010/0082254 | A1* | 4/2010 | Benischek ............ E21B 47/113 702/6 |
| 2011/0127031 | A1 | 6/2011 | Zolezzi Garreton |
| 2014/0010046 | A1* | 1/2014 | Brune .................... E21B 43/26 367/75 |
| 2014/0190691 | A1 | 7/2014 | Vinegar et al. |
| 2015/0356521 | A1* | 12/2015 | Sridhar ............ G06Q 10/06316 705/305 |
| 2015/0369693 | A1 | 12/2015 | Morris et al. |

* cited by examiner

SYSTEM, METHOD, AND FOR IMPROVING OILFIELD OPERATIONS

This application claims the benefit of priority of U.S. provisional application Ser. No. 62/286,397 filed on Jan. 24, 2016, the disclosure of which is herein incorporated by reference in its entirety.

TECHNICAL FIELD

Generally, the present disclosure relates to systems, apparatus and methods for determining ground movement and/or the presence of gases or particulate in the air proximate to a particular ground based area. More specifically, the present disclosure relates to systems, apparatus and methods for monitoring and improving oilfield operations.

DESCRIPTION OF ILLUSTRATIVE EMBODIMENTS

Figure 1:
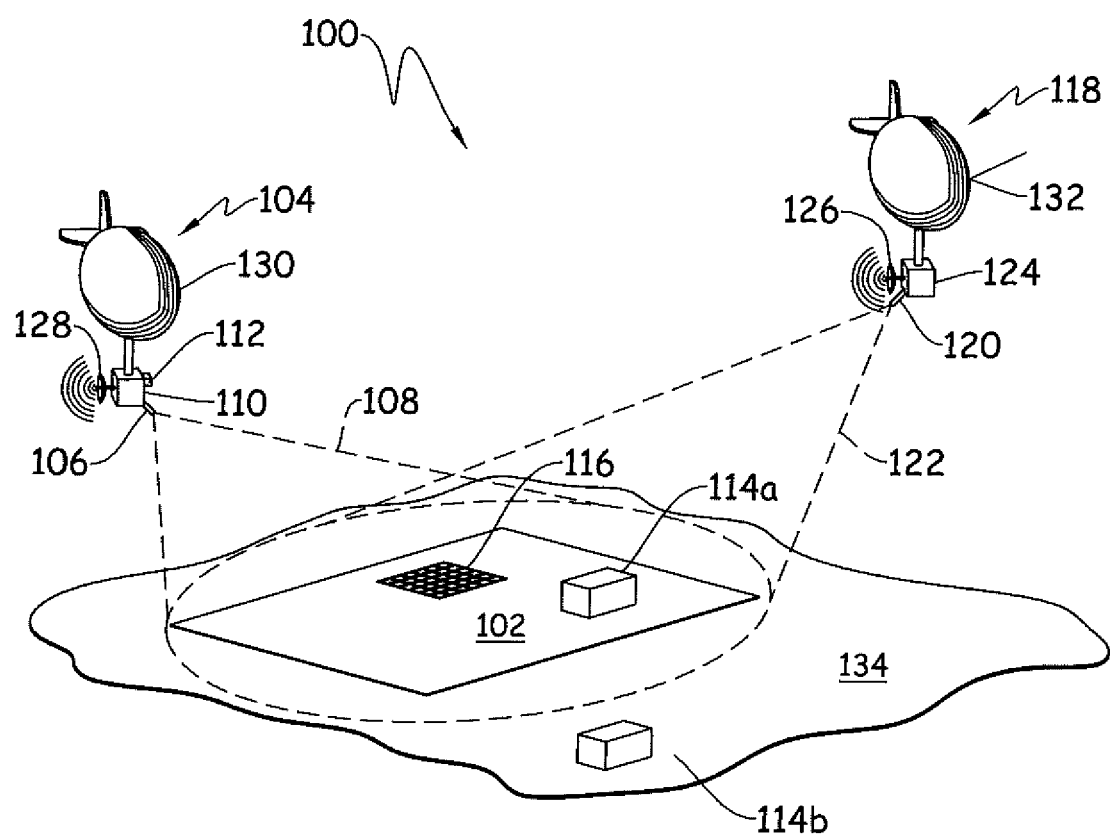
FIG. 1 is a perspective view of an embodiment of the present disclosure.

For the purposes of promoting an understanding of the principles of the invention, reference will now be made to specific embodiments illustrated in the drawings and specific language will be used to describe the same. It will nevertheless be understood that no limitation of the scope of the invention is thereby intended, and any alterations and further modifications in the illustrated embodiments, and any further applications of the principles of the invention as illustrated therein as would normally occur to one skilled in the art to which the invention relates are contemplated herein.

An example system 100 for determining a movement profile of a ground based area is depicted schematically in FIG. 1. The system 100 includes a ground based area 102. The ground based area 102 is described as "ground based" for purposes of convenient description. However, "ground" as used herein is to be understood broadly, and is understood to include any reference surface, whether terrestrial, natural, manufactured, or the like. Non-limiting ground-based areas 102 include, without limitation, a ground area (e.g. earth, rock, etc.), a building, a bridge, a parking lot, a water surface (a lake, pond, pool, bay, section of ocean, fluid reservoir, a tubular extending from a well head, a well head, a treating line fluidly coupled to a well head, an earth based location, an artificial structure, a speaker, a portion of a ground based area etc.), and/or combinations of these. An example ground based area 102 is an area within a larger area 134, which may be the same or a distinct material from the ground based area 102, for example the ground based area 102 may be a location of interest within the larger area 134.

The system 100 further includes an electromagnetic (EM) interrogation device 104 having an EM emitter 106 that directs an EM beam 108 at the ground based area 102. The EM beam 108, in certain embodiments, is an EM beam having a phase and frequency structured to interrogate the ground based area 102 and provide motion information about the ground based area 102. Example and non-limiting EM beams 108 include coherent light (LIDAR) and/or laser LADAR beams. Example EM beams 108 include a selected waveform, such as a laser waveform, and further including without limitation a pulse doublet, a frequency modulated waveform, a chirped waveform, and/or a random or pseudo-random coded waveform. A frequency "chirped" waveform can be chirped in one or both directions—for example with a saw-tooth waveform with increasing or decreasing frequency. Example and non-limiting waveform selection examples include waveform selections to enhance range resolution or range precision, waveform selections to perform unambiguous range determination, waveform selections to positively identify which returning EM radiation reflection corresponds to which emitted EM radiation pulse, and/or waveform selections to enhance velocity determination precision or resolution.

The system 100 further includes a detector array 110 that receives reflected EM radiation from the EM beam 108. An example detector array 110 is a grid of optical detection pixels, and may receive reflected EM radiation through the same aperture or a distinct aperture from the one used in emitting the EM beam 108. The detector array 110 is depicted in the same line of sight as the EM beam 108 with the ground based area 102 for convenience of description, however a beam splitter or other optical device may be utilized wherein the detector array may be alternatively arranged. Any arrangement of the detector array 110 and EM emitter 106 is contemplated herein.

The system 100 is described for convenience having a detector array 110 that conceptually scans the ground based area 102 with an array consisting one or more detectors. Each detector can for example generate a two dimensional pixel, or a 3 dimensional voxel, as well as measuring velocity. Relative intensity can also be measured, sometimes called gray scale. Color can be measured in each pixel of voxel. It is contemplated herein that a system 100 may include multiple range returns within a pixel, for example providing multiple 3 dimensional voxels within a single angle/angle pixel location (e.g. one voxel with a range of the first return, a second voxel with a range of the second return, etc.). One of skill in the art having the benefit of the disclosure herein can readily configure a system 100 to use pixels, voxels, or other imaging description techniques, and these are not limiting to the system 100.

An example system 100 includes the EM beam 108 illuminating a large area of the ground based area 102, and the detector array 110 receiving reflected EM radiation from the entire illuminated area and/or scanned and/or stepped star portions of the illuminated area—for example covering 32×32 detectors, or 128×128 pixels or the like. An example implementation includes stepping the area viewed by a focal plane array based camera ten (10) times in one direction, or in a 3×4 pattern of the illuminated area. Another example includes utilizing a linear array of detectors 110 covering all or a portion of the illuminated region, and then scanning the linear array. Another example includes utilizing a 2-D pixel array of detectors 110, such as 128 in the cross scan direction by 10 in the scan direction, and scanning in the scan (10) direction, adding movement information each time the detectors 110 collect EM reflection information. An example including ten detectors 110 would include sampling the scan direction ten (10) times.

The system 100 further includes a controller 112. The system includes a controller having a number of modules structured to functionally execute operations to detect and characterize ground motion of the ground based area 102. Any controller described herein forms a portion of a processing subsystem including one or more computing devices having memory, processing, and communication hardware.

Each controller may be a single device or a distributed device, and the functions of each controller may be performed by hardware and/or as computer instructions on a non-transient computer readable storage medium.

In certain embodiments, a controller includes one or more modules structured to functionally execute the operations of the controller. The description herein including modules emphasizes the structural independence of the aspects of the controller, and illustrates one grouping of operations and responsibilities of the controller. Other groupings that execute similar overall operations are understood within the scope of the present application. Modules may be implemented in hardware and/or as computer instructions on a non-transient computer readable storage medium, and modules may be distributed across various hardware or computer based components.

Example and non-limiting module implementation elements include sensors providing any value determined herein, sensors providing any value that is a precursor to a value determined herein, datalink and/or network hardware including communication chips, oscillating crystals, communication links, cables, twisted pair wiring, coaxial wiring, shielded wiring, transmitters, receivers, and/or transceivers, logic circuits, hard-wired logic circuits, reconfigurable logic circuits in a particular non-transient state configured according to the module specification, any actuator including at least an electrical, hydraulic, or pneumatic actuator, a solenoid, an op-amp, analog control elements (springs, filters, integrators, adders, dividers, gain elements), and/or digital control elements.

Figure 2:
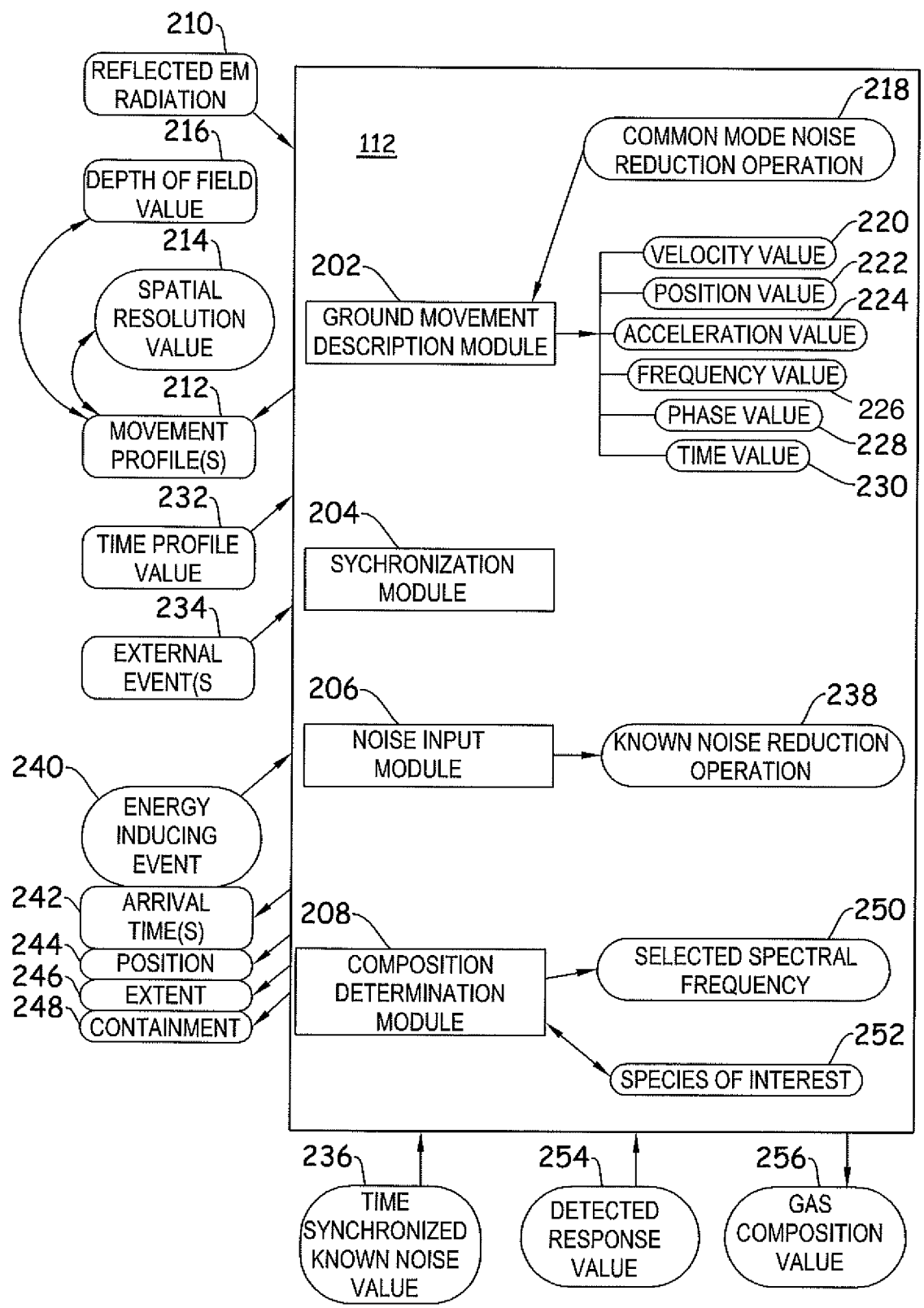
FIG. 2 is a representation of the controller modules, inputs and flows of the present disclosure.

Referring to FIG. 1 and FIG. 2, hardware and/or process implementations included in any one or more of the modules described herein, including the ground movement description module 202, the synchronization module 204, the noise input module, 206, and the composition determination module 208 may include, without limitation, a LIDAR device, a LADAR device, a laser radar device, an EM emitter, an EM receiver, one or more receiving apertures, a synthetic aperture EM emitter and receiver (synthetic aperture radar—SAR, or a synthetic aperture lidar—SAL), an inverse SAR or inverse SAL, and/or one or more receiving detector or pixel grids. Additionally or alternatively, hardware and/or process implementations in one or more modules may include a 1-D, 2-D, and/or 3-D EM detection and receiving devices. Additionally or alternatively, hardware and/or process implementations included in one or more modules may include a coherent EM detection and receiving device, a polarized EM detection and receiving device, an EM detection and receiving device with a polarization splitter, a differential absorption EM detection and receiving device, a Laser Induced Breakdown Spectroscopy (LIBS) device, a Laser Induced Fluorescence (LIF) device, and/or an EM detection an receiving device using polarization as a discriminate to distinguish between materials and/or surfaces. Additionally or alternatively, hardware and/or process implementations included in one or more modules may include an active multispectral EM emitter and receiver device, a non-mechanical steerable EM emitter (e.g. a phased array, or phased array of phased arrays LIDAR), a multiple-input multiple-output (MIMO) EM emitter and receiver device, an EM detection and receiving device using a local oscillator (LO) to detect the received phase and amplitude of an EM field, a heterodyne EM detection and receiving device (a temporal heterodyne and/or a spatial heterodyne device), a Gaussian EM emitter, and/or a super-Gaussian EM emitter, or an EM emitter with a shaped, or a different, emission pattern.

Additionally or alternatively, hardware and/or process implementations in one or more modules may include a GPS, an oriented GPS and/or compass, an aiming gimbal, a fast-steering mirror, a Risley prism and/or grating, a polygon scanning mirror, a liquid crystal steering device, an electrowetting steering device, a steerable electro-evanescent optical refraction device, a polarization birefringent grating beam steering device, a liquid crystal polarization grating steering device (single or multiple stages), a lenslet-based beam steering device, an electronically written lenslet steering device, and/or a mixed lenslet array steering device. Additionally, or alternatively, modules may be constructed to be in communication with and/or to receive non-transient information from any of these.

Additionally or alternatively, modules may include processing operations to extract field amplitude and phase information from multiple interferograms, to make skew and/or trapezoid corrections, to make corner cube corrections (dihedral or trihedral), to make speckle corrections, to make atmospheric absorption corrections, atmospheric scattering corrections, atmospheric turbulence corrections, aero-optical effects corrections, signal-to-noise corrections (e.g. thermal noise, shot noise, background noise, and dark current noise), adjustments to improve heterodyne mixing efficiency, pulse coding (for noise correction, unambiguous range determination, etc.), and/or range measurement processing of the EM pulse information. Additionally or alternatively, modules may include processing operations to make corrections include analytical operations to correct for observed effects, and/or hardware selection choices to mitigate predicted and/or observed effects for a given system 100 and ground based area 102.

Certain operations described herein include operations to interpret or determine one or more parameters. Interpreting or determining, as utilized herein, includes receiving values by any method known in the art, including at least receiving values from a datalink or network communication, receiving an electronic signal (e.g. a voltage, frequency, current, or pulse-width modulated PWM signal) indicative of the value, receiving a computer generated parameter indicative of the value, reading the value from a memory location on a non-transient computer readable storage medium, receiving the value as a run-time parameter by any means known in the art, and/or by receiving a value by which the interpreted parameter can be calculated, and/or by referencing a default value that is interpreted to be the parameter value.

Referencing FIG. 2, the controller 112 includes a ground movement description module 202 that determines a movement profile 212 of the ground based area 102 in response to the reflected EM radiation 108. Example and non-limiting implementations of the ground movement description module 202 include hardware, processing, and/or operations to query the ground based area 102 with EM radiation, to determine the movement of the ground based area 102 during a time of interest, and to construct the movement profile 212 in response to the movement of the ground based area 102 during the time of interest. In certain embodiments, the movement profile 212 is constructed from spatial displacement of the ground based area 102, from the velocity of the ground based area 102, from the acceleration of the ground based area 102, from frequency information included in the movement of the ground based area 102, from vibration information included in the movement of the ground based area 102, and/or from one or more of these included in portions of the ground based area 102 from one or more locations of the ground based area 102 and/or at the same location within the ground based area 102.

An example movement profile 212 includes a velocity value 220 of the ground based area 102. For example, the ground movement description module 202 calculates whether any portion of the ground based area 102 is in motion during the time of observation, and reports the velocity value 220 of the motion as the movement profile 212. The example velocity value 220 is reported for any portion of the ground based area 102 at a selected spatial resolution (e.g. the "X-Y" plane relative to the detector array 110) according to the capability of the EM beam 108 and detector array 110, potentially the processing capability available to the processing subsystem of the system 100, as well as the underlying principles of the observed aspect of the ground based area 102. The example velocity value 220 is reported for any portion of the ground based area 102 at a selected depth of field 216 resolution (e.g. the "Z" plane relative to the detector array 110) according to, without limitation, the capability of the EM emitter 106 and EM beam 108, the selected phase and frequency of the EM beam 108, and/or the use of certain techniques such as the use of a local oscillator (LO) to enhance the depth of field 216 resolution capability.

The velocity value 220 of the motion reported as the movement profile 212 may be any velocity value understood in the art that is relevant to the system of interest, and will be dependent upon the underlying principles of operation of the system and the reason for observing the ground based area 102. Example considerations include, without limitation, a velocity value 220 of the ground based area 102 consistent with degradation of a component of the system, a velocity value 220 consistent with a successful treatment operation, a velocity value 220 consistent with a mechanical failure of a component of the system, a velocity value 220 consistent with a loss of fluid or hydraulic containment, a velocity value 220 consistent with an intentionally induced mechanical stress, and/or velocity values 220 consistent with imminent incidents of the foregoing. Example and non-limiting velocity values 220 includes a maximum observed value of the velocity, an averaged value of the velocity over any portion of the observation period and/or throughout the observation period, a root-mean-squared value of the velocity for any statistically relevant portion of the observed velocity values, a sequence of corresponding time and velocity paired values (e.g. a velocity plot or equivalent stored data), and/or any other description of the velocity value 220. One of skill in the art, having an understanding of the system ordinarily available, and the benefit of the disclosure herein, will readily understand velocity values 220 to include in a movement profile 212.

An example controller 112 includes the ground movement description module 202 that determines the movement profile 212 in response to a position value 222, 348 of the ground based area 102. For example, the ground movement description module 202 calculates whether any portion of the ground based area 102 has moved or been displaced during the time of observation, and reports the position value 222, 348 of the ground based area 102 as the movement profile 212. The example position value 222, 348 is reported for any portion of the ground based area 102 at a selected resolution according to the capability of the EM beam 108 and detector array 110, potentially the processing capability available to the processing subsystem of the system 100, as well as the underlying principles of the observed aspect of the ground based area 102.

Example considerations include, without limitation, a position value 222, 348 of the ground based area 102 consistent with degradation of a component of the system, a position value 222, 348 consistent with a successful treatment operation, a position value 222, 348 consistent with a mechanical failure of a component of the system, a position value 222, 348 consistent with a loss of fluid or hydraulic containment, a position value 222, 348 consistent with an intentionally induced mechanical stress, a position value 222, 348 consistent with a depletion of an amount of fluid in a fluid reservoir, a position value 222, 348 utilized to provide a surface description in response to the movement profile, and/or to provide a subsystem volume in response to the surface description, and/or position values 222, 348 consistent with imminent incidents of the foregoing.

Example and non-limiting position values 222 include a maximum observed value of the position, an averaged value of the position over any portion of the observation period and/or throughout the observation period, a root-mean-squared value of the position for any statistically relevant portion of the observed position values, a sequence of corresponding time and position paired values (e.g. a position plot or equivalent stored data), and/or any other description of the position value 222. One of skill in the art, having an understanding of the system ordinarily available, and the benefit of the disclosure herein, will readily understand position values 222 to include in a movement profile 212.

An example controller 112 includes the ground movement description module 202 that determines the movement profile 212 in response to an acceleration value 224 of the ground based area 102. For example, the ground movement description module 202 calculates whether any portion of the ground based area 102 experiences an acceleration event during the time of observation, and reports the acceleration value 224 of the ground based area 202 as the movement profile 212. The example acceleration value 224 is reported for any portion of the ground based area 102 at a selected spatial resolution (e.g. the "X-Y" plane relative to the detector array 110) according to the capability of the EM beam 108 and detector array 110, potentially the processing capability available to the processing subsystem of the system 100, as well as the underlying principles of the observed aspect of the ground based area 102. The example acceleration value 224 is reported for any portion of the ground based area 102 at a selected depth of field 216 resolution (e.g. the "Z" plane relative to the detector array 110) according to, without limitation, the capability of the EM emitter 106 and EM beam 108, the selected phase and frequency of the EM beam 108, the use of certain techniques such as the use of a local oscillator (LO) to enhance the phase and/or velocity information, and/or the execution rates of the acceleration determination operations and the processing power committed to the acceleration determination operations.

The acceleration value 224 of the motion reported as the movement profile 212 may be any acceleration value understood in the art that is relevant to the system of interest, and will be dependent upon the underlying principles of operation of the system and the reason for observing the ground based area 102. Example considerations include, without limitation, an acceleration value 224 of the ground based area 202 consistent with degradation of a component of the system, an acceleration value 224 consistent with a successful treatment operation, an acceleration value 224 consistent with a mechanical failure of a component of the system, an acceleration value 224 consistent with a loss of fluid or hydraulic containment, an acceleration value 224 consistent with an intentionally induced mechanical stress, and/or velocity values 220 consistent with imminent incidents of the foregoing.

Example and non-limiting acceleration values 224 include a maximum observed value of the acceleration, an averaged value of the acceleration over any portion of the observation period and/or throughout the observation period, a root-mean-squared value of the velocity for any statistically relevant portion of the observed acceleration values, a sequence of corresponding time and acceleration paired values (e.g. an acceleration plot or equivalent stored data), and/or any other description of the acceleration value 224. One of skill in the art, having an understanding of the system ordinarily available, and the benefit of the disclosure herein, will readily understand acceleration values 224 to include in a movement profile 212.

An example controller 112 includes the ground movement description module 202 that determines the movement profile 212 in response to a frequency value 226 of the ground based area 102. For example, the ground movement description module 202 calculates frequency values 226 in the movement of the ground based area 102, and provides the movement profile 212 in response to the frequency values 226. Non-limiting examples include determining frequency based information from any device or subsystem in stress communication with the ground based area 102. For example and without limitation, identification of equipment, detection of degradation of equipment and/or devices, passing of communication signals, determination of event occurrences and types, are all potential uses of the movement profile 212 from the frequency value 226 by one of skill in the art having the benefit of the disclosures herein. The movement profile 212 may be constructed from the frequency value 226 utilizing frequency deconvolution techniques such as, without limitation, Fourier transforms, fast Fourier transforms (FFTs), high speed sampling, and/or the frequency values 226 may be utilized directly without deconvolution of the movement values of the ground based area 102.

An example operation to utilize the frequency values 226 to provide the movement profile 212 includes determining an amplitude of a movement of a portion of the system 100 in response to 1) understanding an expected contribution of the portion of the system (e.g. due to a resonant frequency or operating frequency of the portion of the system), 2) detecting the actual contribution of the portion of the system (e.g. detecting the actual contribution at the resonant frequency or operating frequency by observing the area where the portion of the system would cause movement, and performing an FFT to see if movement is occurring at the expected frequency), and 3) comparing the expected contribution to the actual contribution to determine if (a few examples): the equipment is operating properly, or if the bridge is deflecting more than expected, or if the equipment has not yet been activated, or if one of the cylinders is not operating properly, etc.

Example and non-limiting operations to utilize the frequency values 226 to provide the movement profile 212 include: determining messages from a frequency modulated signal, determining that a movement is not a background or noise movement in response to a frequency value 226, backing out a noise component from the movement in response to a frequency value 226, backing out a known noise component from the movement in response to a known frequency value 226, and/or backing out a common mode noise component that occurs in both a first EM detection device 104 and a second EM detection device 118 at a particular frequency value 226.

An example controller 112 includes the ground movement description module 202 that determines the movement profile 212 in response to a phase value 228 of the ground based area 102. For example, the ground movement description module 202 calculates phase values 228 in the movement of the ground based area 102, and provides the movement profile 212 in response to the phase values 228. Non-limiting examples include determining phase based information from any device or subsystem in stress communication with the ground based area 102. For example and without limitation, identification of equipment, detection of degradation of equipment and/or devices, passing of communication signals, determination of event occurrences and types, are all potential uses of the movement profile 212 from the phase value 228 by one of skill in the art having the benefit of the disclosures herein.

An example operation to utilize the phase value(s) 228 to provide the movement profile 212 includes determining an amplitude of a movement of a portion of the system 100 in response to 1) understanding an expected contribution of the portion of the system (e.g. due to a phase contribution of the portion of the system, e.g. by the number of cylinders and/or phases of a pump contributing thereto), 2) detecting the actual contribution of the portion of the system (e.g. detecting the individual pulses of the portion of the system and the phases thereof), and 3) comparing the expected contribution to the actual contribution to determine if (a few examples): the equipment is operating properly, or if the equipment has not yet been activated, or if one of the cylinders is not operating properly, etc.

An example controller 112 includes the ground movement description module 202 that determines the movement profile 212 in response to a time value 230 of the ground based area 102. For example, the ground movement description module 202 calculates phase values 228 in the movement of the ground based area 102, and provides the movement profile 212 in response to the phase values 228. For example, and without limitation, the ground movement description module 202 determines an expected progress of the movement profile 212 over time, and/or monitors that no movement has occurred as expected over time, and determines whether a treatment or operation is successful or has failed in response to the movement profile 212.

An example controller 112 further includes a synchronization module 204 that interprets a time profile value 232 corresponding to an external event 234, and synchronizes the determining of the movement profile 212 to the external event 234. The synchronizing the movement profile 212 to the external event 234 can include, without limitation, correcting the detection array 110 such that the movement profile 212 is created independent of the external event 234, and/or creation of the movement profile 212 recognizing the effect of the external event 234 on the movement profile 212. Example and non-limiting external events 234 include external events that induce a mechanical stress that are in mechanical stress coupling to the ground based area 102, such as but not limited to construction events, pumping events, seismic events, underground events (not shown), and/or other events known in the art. External inducing equipment may be within the ground based area such as on-location inducing equipment 114a, or outside the ground based area such as remote inducing equipment 114b, and may communicate directly with the controller 112, or may communicate indirectly—for example by operating in an agreed upon schedule or manner. In certain embodiments, the ground movement description module 202 further relates at least a portion of the movement profile 212 to the external event 234 in the time domain.

In certain embodiments, the system 100 includes an energy inducing device operationally coupled to the ground based area 102, such as the on-location inducing equipment 114a and/or the remote inducing equipment 114b, and the ground movement description module is further determines the movement profile 212 in response to an energy inducing event 240 from the energy inducing device 114a, 114b. Example and non-limiting determinations of the movement profile 212 from the energy inducing events 240 include determining: at least one arrival time 242 from the entering inducing device, a position 244 of the energy inducing event 240, an extent 246 of the energy inducing event, and/or a containment 248 (or lack thereof) of the energy inducing event. An example energy inducing devices includes an explosive device, such as an explosive utilized in demolition, construction, road building, a seismic source, a thumper truck, and/or a perforating tool. Another example energy inducing device includes a hydraulic hammer (e.g. a seismic source) or other hydraulic and/or pneumatic device, a sonic device, an ultrasonic device, an electrically operated device, a pneumatically operated device, a hydraulic inducement, and/or a hydraulically operated device. The energy inducements listed may be the initial energy source listed, and/or may be the inducement energy source, with a prime mover such as an internal combustion engine or the like driving the inducement energy source. The term "energy inducing device" 114a, 114b should be understood broadly to be any device capable of mechanically engaging the ground based area 102 in a manner sufficiently to be detectable as movement by the EM interrogation device(s) 104, 118, either through deliberate operations of the energy inducing devices 114a, 114b, and/or as a byproduct of other operations of the energy inducing devices 114a, 114b.

An example system 100 further includes the ground movement description module 202 determining the movement profile 212 in response to an energy inducing event 240 by determining an extent 246 of the inducing, where the extent 246 of the inducing is a spatial extent. An example extent 246 of the inducing includes an X-Y description of an area affected by the energy inducing event 240. Another example extent 246 of the inducing includes an indicator that the energy inducing event has exceeded a threshold extent value. In certain embodiments, the threshold extent value can be an azimuthal threshold value, for example an X directional value, a Y directional value, or some radial angle value in the X-Y plane, and/or the extent can be a Z-directional value, such as an indication that a given area of the ground based area 102 has raised beyond a threshold value, and/or that some movement has occurred consistent with movement somewhere else in the system 100. The provided examples determining the extent 246 values are non-limiting examples, and combinations of these, and/or other extent values understood to one of skill in the art having the benefit of the disclosures herein, are contemplated herein.

An example system 100 includes the ground movement description module 202 determining the movement profile 212 in response to an arrival time(s) 240 following the energy inducing event 242. For example, an energy inducing device 114b may be in communication with the EM interrogation device 104, and/or the devices 104, 114b may otherwise be synchronized, such that the ground movement description module 202 is able to determine an observed time lag between the energy inducing event 240 and the arrival of movement consistent with resulting pressure waves (P-waves) and shear waves (S-waves). Additionally or alternatively, a signal may be introduced to the energy inducing event 240 such that the start time between at least two energy inducing events may be induced from the event itself—for example through a sequenced set of energy events, or the like.

An example system 100 includes the ground movement description module 202 determining the movement profile 212 in response to a position 244 of the energy inducing event 240. For example, an exact location of a perforating event in a horizontal wellbore may be unknown, and a position within the ground based area 102 experiencing the greatest acceleration, velocity, and/or positional movement at a time of firing of the perforating gun may be estimated to be the position of the perforating gun at the time of firing. The information provided by the ground movement description module 202 may be combined with other information available, such as how far the tool has run in the wellbore (not shown), how deep the well is, the angle and wellbore trajectory, etc., to provide an estimate of the position of the perforating gun at the time of firing. Additionally or alternatively, the position 244 of the energy inducing event 240 may be a position of an injection into a formation, of a wellbore screenout event, of a failing pump, of a failing piece of equipment, of a degrading piece of equipment, confirmation of correct placement of an energy inducing device 114a, 114b, and/or identification of equipment layout at a location (e.g. by confirming placement of several energy inducing devices 114a).

An example system 100 includes the ground movement description module 202 determining the movement profile 212 in response to a containment value 248 of the energy inducing event 240. An example includes determining that the energy inducing event 240 has not broken out of a designated zone—for example that movement of the ground based area 102 is consistent with zone containment in a hydraulic fracture treatment for a shallow horizontal shale or coal bed methane well. In certain embodiments, the controller 112 is in communication with the energy inducing device 114a, and upon detecting movement of the ground based area 102 consistent with a loss of containment or an imminent loss of containment, the controller 112 can communicate with the energy inducing device 114a and/or an operator thereto to take corrective actions to prevent or mitigate the loss of containment. Example and non-limiting actions include a reduction in the pumping rate, stopping pumping operations, and/or a reduction in the fluid viscosity being pumped into the formation.

In certain embodiments, the movement profile 212 includes a spatial resolution value 214 of not greater than 1 square foot pixels, a spatial resolution value of not greater than 1 square inch pixels, and/or a spatial resolution value of not greater than 1 square centimeter pixels. The range precision measured in each pixel may be a value no greater than 0.1 mm, or no greater than 1 mm, or no greater than 1 cm, or no greater than 1 inch, or no greater than 1 foot. Range resolution values may be no greater than 0.1 mm, or no greater than 1 mm, or no greater than 1 cm, or no greater than 1 inch, or no greater than 1 foot. Referencing FIG. 1, a grid 116 is illustrated on the ground based area 102 depicting a portion of the ground based area 102 showing an illustrative resolution of the area. The selection of a spatial resolution value 214 depends upon the purpose for determining the movement profile 212, and modern EM interrogation devices 104, 118 known to those of skill in the art are fully capable of resolutions of 1 cm or even smaller if the purpose of the system 100 makes such resolution desirable. Determination of hydraulic fracture lengths on the order of hundreds of feet may not require a resolution of but 1 square foot or even greater. Determination of a bridge failure location with the best possible resolution, or attempting to identify movement in separate treating lines from one another—which may be several inches across—may lead one of skill in the art to select a spatial resolution of 1 square cm. One of skill in the art, having the benefit of the disclosures herein, can select a detector array 110 and appropriate processing equipment 112 to develop the desired spatial resolution value 214 for a particular system 100.

An example system 100 includes a number of EM interrogation devices 104, 118. Each device 104, 118 includes an EM emitter 106, 120, and each emitter 106, 120 directs at least one EM beam 108, 122 to the ground based area 102. Each EM interrogation device 104, 118 further includes a detector array 110, 124 which receives reflected radiation 210 from the ground based area 102, which may be received through the same or a distinct aperture from the aperture utilized by the emitter 106, 120. The detector array 110, 124 may receive reflected radiation from a beam splitter, or may be somewhat remotely located from the emitter 106, 120, as will be understood to those skilled in the art. Each EM interrogation device 104, 118 in the example further includes a transceiver 126, 128 for providing wireless communications to and from a controller 112, 124, although the controllers 112, 124 may be in communication with other portions of the system 100 by any other communication devices understood in the art.

The controllers 112, 124, as described above, form a portion of a processing subsystem, and may be distributed devices and/or combined. The controllers 112, 124 may be on the EM interrogation devices 104, 118 as depicted in FIG. 1, in whole or part, or may be remote from the EM interrogation devices. The controllers 112, 124 are in operative communication with any sensor and/or actuator in the system 100 as needed to perform any operations of the controllers described herein.

The EM interrogation devices 104, 118 are schematically depicted in FIG. 1 as being deployed on dirigibles, which may be positioned by GPS. However, the EM interrogation devices 104, 118 may be positioned at the location 134 above the ground based area 102 in any fashion, including at least on a tower, on a boom, on a drone, on an unmanned air vehicle (UAV), on a helicopter, on a tethered or untethered balloon, on a rig, and/or on any structure that is already present at the location 134. While being present on a stationary or a controlled-movement object is helpful, the EM interrogation devices 104, 118 can be positioned on a moving object, as the controller 112, 124 can correct for movement—including flight such as from a plane, a UAV, drone, or unmanned air vehicle. Additionally, while being closer to straight above the ground based area 102 is helpful, the controller 112, 124 can correct for skew, including a significant amount of skew exceeding 45 degrees from the horizontal. Additionally, in certain embodiments the EM interrogation devices 104, 118 may be in position only intermittently during the observation period and still build a movement profile 212 of the ground based area 102.

In certain embodiments, the EM interrogation devices 104, 118 corresponding to a number of EM emitters 106, 120, each directing a corresponding EM beam 108, 122 at the ground based area, and each having a corresponding detector array 110, 124 that receives reflected EM radiation 210 from the corresponding EM beams. The controllers 112, 124 each have a ground movement description module 202 that determines a movement profile 212 of the ground based area 102 in response to the reflected EM radiation from each of the corresponding EM beams 108, 122. The system 100 further includes the ground movement description module 202 determine the movement profile 212 in response to a common mode noise reduction operation 218. For example, the ground movement description module 202 rejects and/or reduces noise appearing on both detector arrays 110, 124—which may include checking for time phase lag, etc. if such is sensible for the physical system (e.g. the EM emitters 106, 120 are differentially spaced, and a 0.25 seconds of lag is appearing in a common mode noise).

The example system 100 further includes the controllers 112, 124 having a noise input module 206 that interprets a time synchronized known noise value 236 where the ground movement description module 202 further determines the movement profile 212 in response to a known noise reduction operation 238 performed in response to the time synchronized known noise value 238. For example, the energy inducing devices 114a may have a superficial surface disturbance on a planned schedule that is known to disturb the surface in a known way, and the noise input module 206 will input the planned schedule as the known noise reduction operation 238 to either ignore those time periods and/or correct for them in a known manner. Non-limiting examples include demolition operations, pumping operations, drilling operations, etc.

An example system 100 further includes a gas composition detector (not shown—but it can share the same equipment with the EM emitter 106) that interrogates an air volume in proximity to the ground based area 102 with an EM radiation including at least a selected spectral frequency value 250, a second detector array (not shown) structured to receive the reflected EM radiation 210 having the selected spectral frequency value 250 and to provide a detected response value 254, and where the controller 112 further includes a composition determination module 208 that determines a gas composition value 256 in response to the detected response value 254.

A fraction of a laser or coherent light will reflect off the atmosphere back to a detector, and in one example if the light includes a reference frequency or wavelength which does not substantially absorb, along with light having frequencies within an absorption spectrum for a species of interest 252, then an absorption differential can determine the gas composition value 256. In another example a fraction of the laser or coherent light passes through the atmosphere and reflects off the ground or other object having a more uniform spectral response then the atmosphere the light passes through. If the reflectivity of the object light reflects from after traversing the atmosphere has lower spectral change then the absorption from passing through the atmosphere to the reflector and back, then the differential return can be used to determine the gas composition value 256. In certain embodiments, the gas composition value 256 includes an indication of the species of interest 252 in the air volume in proximity to the ground based area 102. In certain further embodiments, the species of interest includes $CO_2$, $H_2S$, a natural gas component, and/or a tracer material. In certain embodiments, the natural gas component includes a hydrocarbon species having between 1 and 4 Carbons. In certain embodiments, the tracer material includes a material included in a wellbore treatment.

An example system includes the movement profile 212 having a depth of field value 216 with a resolution of not greater than 1 mm.

It will be understood by one of skill in the art, having the benefit of the disclosures herein, that the disclosures herein provide numerous improvements to various technologies and technological fields. Without limitation, technologies improved include the maintenance, service, and construction of civil engineering projects (buildings, bridges, roads, parking lots), through-solid material communication technologies, the tracking of substrate movement in response to both acute events and over time, and the improved ability to detect the presence of undesired or dangerous substances, or to confirm the presence of desired substances, which is particularly applicable to many civil and geological applications. Without limitation, improved technological fields include civil engineering, construction, geology, land use maintenance, road maintenance, and oil field applications.

The schematic operational descriptions which follow provide illustrative embodiments of performing procedures for determining a movement profile for a ground based area. Operations illustrated are understood to be exemplary only, and operations may be combined or divided, and added or removed, as well as re-ordered in whole or part, unless stated explicitly to the contrary herein. Certain operations illustrated may be implemented by a computer executing a computer program product on a non-transient computer readable storage medium, where the computer program product comprises instructions causing the computer to execute one or more of the operations, or to issue commands to other devices to execute one or more of the operations.

A method includes an operation to direct an electromagnetic (EM) beam at a ground based area, to receive reflected EM radiation from the EM beam at a detector array, and to determine a movement profile of the ground based area. An example method further includes an operation to determine the ground based movement corresponding to at least a portion of the ground based area, the description of the ground based movement including a velocity value, a position value, an acceleration value, a frequency value, a phase value, and/or a time value. An example method further includes an operation to synchronize the determining to an external event, and an operation to relate at least a portion of the movement profile to the external event in the time domain.

An example method further includes an operation to induce a ground energy event, where the operation to determine the movement profile of the ground based area is in response to the inducing. A further example method includes an operation to determine at least one arrival time event, an operation to determine a position of the inducing, an operation to determine an extent of the inducing, and/or an operation to determine a containment of the inducing.

An example method includes an operation to determine the movement profile with a spatial resolution not exceeding: greater than 1 square foot pixels, greater than 1 square inch pixels, and/or greater than 1 square centimeter pixels. An example method includes an operation to determine a number of movement profiles from a corresponding number of detector arrays positioned around the ground based area. An example method includes an operation to determine the movement profile by performing a common mode noise operation, and/or by interpreting a time synchronized known noise value and performing a known noise reduction operation in response to the time synchronized known noise value.

An example method includes an operation to interrogate an air volume in proximity to the ground based area with EM radiation including at least a selected spectral frequency value, an operation to receive reflected EM radiation from the EM radiation including the selected spectral frequency value, and an operation to determine the presence of a species of interest in the air volume in response to the reflected EM radiation. A further example method includes the species of interest being $CO_2$, $H_2S$, a natural gas component, and/or a tracer material.

An example method includes an operation to determine movement of a ground-based area, including illuminating the ground-based area with an electro-magnetic (EM) radiation device, and receiving reflected EM radiation from the ground-based area in response to the illuminating. The example method further includes processing the reflected EM radiation to determine movement information of at least a portion of the ground-based area in response to the receiving the reflected EM radiation. Example movement information includes at least one of displacement, velocity, acceleration, vibration, and movement frequency information of at least a portion of the ground-based area. The example method includes performing further operations including diagnosing a ground based operation, diagnosing a ground based device, receiving a communication from a device in vibrational communication with the ground-based area, and/or determining a status of a ground based operation in response to the movement information. An example method further includes illuminating the ground-based area with an EM radiation device, such as EM emitter 106, further including operating a differential absorption EM detection and receiving device, a Laser Induced Breakdown Spectroscopy (LIBS) device, and/or a Laser Induced Fluorescence (LIF) device and identifying a species of interest in the air volume in proximity to the ground-based area.

Certain further example systems and methods of the disclosure are described following. Certain details of potential hardware implementations of contemplated systems and methods are omitted in the following description for purposes of clarifying the concepts described therein. One of skill in the art, having the benefit of the disclosure herein, including previously described hardware implementations, can readily prepare hardware implementations of the contemplated systems and methods described herein.

Figure 3:
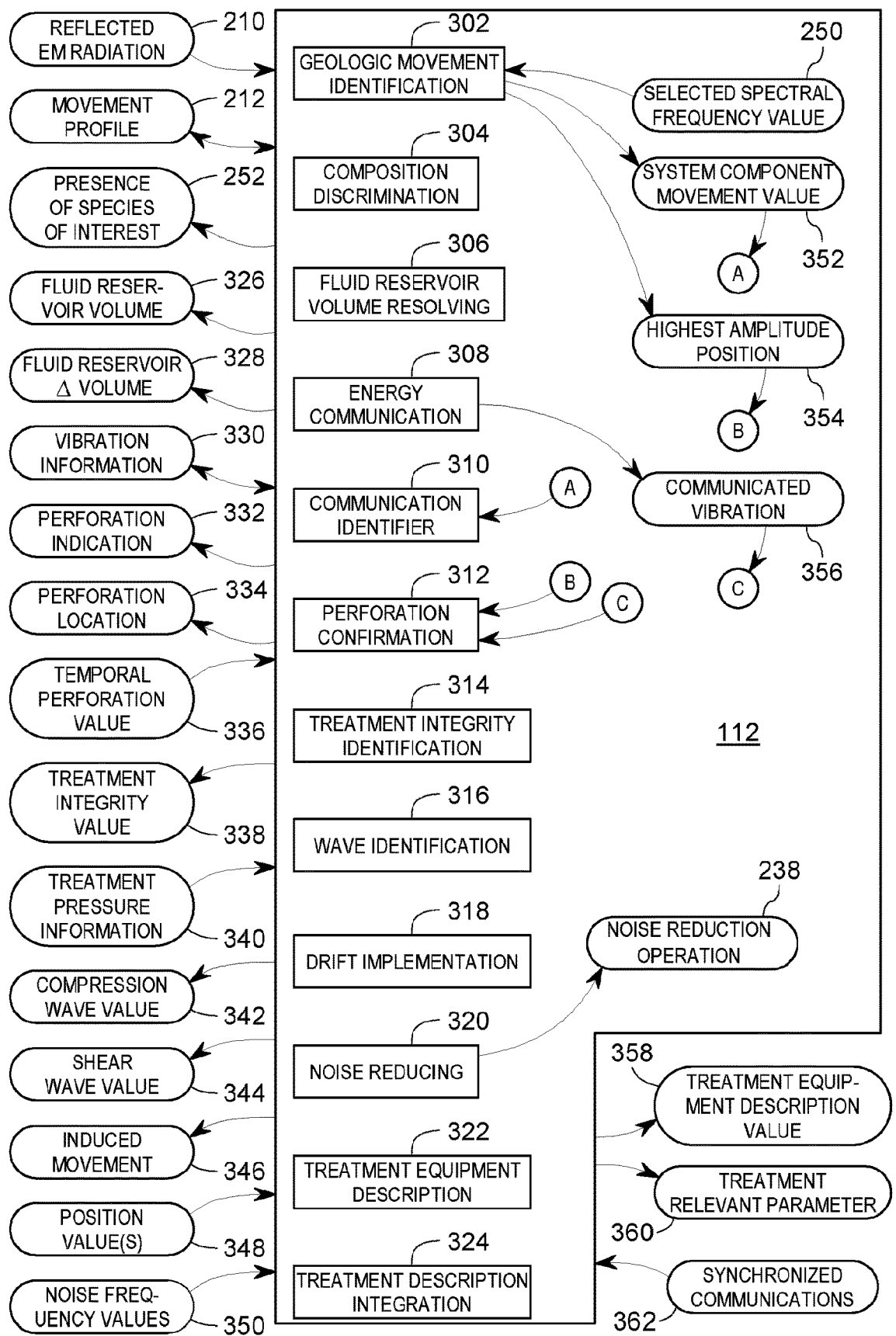
FIG. 3 is a further representation of the controller modules, inputs and flows of the present disclosure.

Referring to FIGS. 1-3, an aspect of the present disclosure includes a system 100 having a geological location 134, an electromagnetic (EM) interrogation device 104 having an EM emitter 106 structured to direct an EM beam 108 at the ground based area 102 of a geological location 134, and having a detector array 110 structured to receive reflected EM radiation 210 from the EM beam 108. The example system 100 further includes a controller 112 having a geologic movement identification circuit 302 structured to determine a movement profile 212 of the geological location 134 in response to the reflected EM radiation 210.

The term circuit used herein should be understood broadly. A circuit includes one or more hardware devices operationally cooperating to perform the operations of the circuit. In certain embodiments, a circuit may include non-transient data stored on a computer readable medium, such as instructions for a computer which causes the computer to perform one or more operations of the circuit. Circuits may additionally or alternatively include any sensors, actuators, or any other hardware to perform the operations of the circuit.

Certain aspects of the present disclosure further include the geological location 134 being at least one of a ground based area 102, such as, an oilfield location, a gas well location, an oil well location, a disposal well location, a water well location, a coal bed methane well location, a shale oil location, a location including a horizontal well, a location including a well fluidly coupled to a hydrocarbon formation having sour hydrocarbons, a location including a well fluidly coupled to a shallow formation, and/or a location including an exploration area—for example an area to be searched for the presence of hydrocarbons, water, or certain geological formations.

Certain aspects of the system 100 include the EM interrogation device 104 being further structured to interrogate an air volume in proximity to the geological location 134 with EM radiation, where the EM radiation includes at least a selected spectral frequency value 250. The EM interrogation device 104 receives reflected EM radiation 210 including the selected spectral frequency value 250, and wherein the controller 112 further comprises a composition discrimination circuit 304 structured to determine the presence of a species of interest in the air volume in response to the reflected EM radiation 210. Example and non-limiting air volumes include a volume where personnel are located, a volume near a wellhead, a volume near treating lines, a volume near a drilling rig, and/or a volume above a fluid reservoir (e.g. a flowback pit, a mud pit, a drilling mud pit, and/or a fluid reservoir fluidly coupled to a treated formation or another formation of interest).

In certain embodiments, the interrogation device 104 is further structured to interrogate the air volume receiving reflected EM radiation 210 from gas molecules present in the air volume, and/or receiving reflected EM radiation 210 that has passed through the air volume. In one example, reflected EM radiation 210 directly from the air volume can show absorption of the selected spectral frequency 250, allowing for the determination of the presence of a species of interest 252 within the air volume.

In another example, reflected EM radiation 210 from an object beyond the air volume (e.g. the ground underneath the air volume) is received that has passed through the air volume. In addition to the presence of the species of interest 252 within the air volume, a concentration of the species of interest 252 may be made, either through statistical analysis of the amount of absorption observed, and/or through determination of the amount of air volume through which the reflected EM radiation 210 has passed along with the observed amount of absorption. In certain embodiments, absorption may be observed with respect to absorption of a normalized species (e.g. $O_2$, $N_2$, $CO_2$, or other species present in known quantities) to determine the concentration of the species of interest 252. The selection of a spectral frequency 250 will be dependent upon several factors, including at least which spectral frequency values are available as sources, which frequencies correlate to absorption peaks in the species of interest and/or normalized species, and the strength of peak that is desirable for detection (e.g. selecting a lower absorbing peak where concentrations may otherwise be high enough for complete absorption). In certain embodiments, one or more ranges of frequencies may be selected that include one or more absorption peak frequencies therein.

In certain embodiments, the species of interest 252 includes $CO_2$, $H_2S$, a natural gas component, a tracer material, a material indicative of a release of a treatment fluid, a material indicative of a release of formation gases, a material indicative of a release of wellhead gases, and/or a material indicative of a release of an energized treatment fluid (e.g. $CO_2$-based or $N_2$-based energized fluids, including surfactants or other constituents that may be present in such fluids or that are expected to be indicative of the release of such fluids). A tracer material may include any material intentionally added for the purpose of detection—for example radioactive materials added that are intended to show up in well logs after a treatment. The determination of a tracer material may include direct determination of a tracer material that absorbs a known EM frequency or wavelength value, and/or determination of a substrate for the tracer material, where the substrate absorbs a known EM frequency value. It can be seen that the present disclosure provides a system and method to detect species of interest 252 in a broad area, at low concentrations, with almost immediate detection. The present disclosure can additionally provide such information as a likely source for the species of interest 252 and/or a concentration gradient of the species of interest 252 at the location 134. By contrast, a system relying upon an ordinary sensor (e.g. an H2S sensor) relies upon proper placement of the sensor, a release of the species to intersect with the sensor, and does not provide any information about the actual source or distribution of the species of interest 252.

An example system 100 includes the geological location 134 being an investigation surface, where the EM interrogation device 104 is further structured to interrogate the investigation surface with EM radiation including at least a selected spectral frequency value 250 and to receive reflected EM radiation 210 including the spectral frequency value. The example system 100 further includes a controller 112 including a composition discrimination circuit 304 that determines the presence of a species of interest 252 on the investigation surface in response to the reflected EM radiation 210. Example and non-limiting species of interest include a treatment fluid, a wellbore fluid, a treatment constituent, an acid, a tracer material, a tracer fluid substrate, and/or a hydrocarbon fluid. It can be seen that the present disclosure provides for a system and method that can detect spills, leaks, or other fluid releases onto surfaces in a broad area, at low concentrations, with almost immediate detection. The present disclosure can additionally provide such information as the likely source for a leak or spill, and information such as a concentration gradient of a species on a surface.

By contrast, presently available systems rely upon either correct placement of a sensor to detect a leak or spill, or upon the diligence of personnel present at the location. The personnel present at the location may not be correctly positioned to detect a leak or spill (e.g. it may be desirable that they stay away from unsafe areas of the location), they may not see the leak or spill due to other duties they have to perform, or they may lack the experience or ability to determine that a leak or spill has occurred. Additionally, previously available leak and spill detection systems may require that a leak or spill is large before it is detected, increasing the damage or other negative consequences of the release.

In certain aspects, the ground based area 102 of a geological location 134 includes a tubular extending from a well head, a well head, a treating line fluidly coupled to a well head, treating equipment positioned at the geological location, an earth based location, an artificial structure, a pump, a fluid pit, and/or a fluid positioned in a fluid pit. The term tubular used herein should be understood broadly, and includes at least a wellbore tubing, a wellbore casing, annuluses thereof, a coiled tubing, and/or a drill string. The example system 100 further includes the controller 112 having a fluid reservoir volume resolving circuit 306 structured to determine a volume of fluid in a fluid reservoir 326 and/or a differential volume of fluid in a fluid reservoir 328. The EM interrogation device 104 can map the 3-dimensional surface of the fluid reservoir in real time, and make a near instantaneous determination of the volume of the fluid 326 therein, or the rate of change of the volume of the fluid therein. The present disclosure provides for a fluid volume 326 determination that is immediate and accurate to an arbitrary degree of resolution.

By contrast, presently available systems depend upon fluid gauges or markings that can be low resolution, ineffective for viscous fluids that have not fully distributed through the reservoir, and that require diligent manual checks. Alternative presently available systems may utilize flow meters that are not accurate in many operating conditions, and that accumulate errors of integration over time resulting in an increasingly inaccurate determination of fluid volume over time. Example and non-limiting fluid reservoirs include a drilling mud pit, a fluid flowback pit, and/or a treatment fluid supply reservoir.

In certain aspects, the system 100 includes an energy communication circuit 308 vibrationally coupled to at least one system component such as a tubular extending from a well head, a well head, a treating line fluidly coupled to a well head, an earth based location, an artificial structure, a speaker, and/or a fluid reservoir. The example energy communication circuit 308 includes at least one of a logging device, an explosive device, a physical impulse device, a measurement while drilling (MWD) device, a logging while drilling (LWD) device, and/or any other physical stimulus device such as a seismic source. An example controller 112 further includes a communication identifier circuit 310 that interprets a communicated vibration 356 from the energy communication circuit 308 in response to at least one value from the geologic movement identification circuit 302. Example and non-limiting values include at least one of a velocity value 220, a position value 222 348, an acceleration value 224, a frequency value 226, a phase value 228, and/or a time value 230 corresponding to the system component. Non-limiting examples of operations of the energy communication circuit 308 include determining movement and/or vibration information from a tubular, drill-string, well head, earth based location, artificial structure, speaker, and/or fluid reservoir, for example utilizing a laser Doppler vibrometer technique on a surface of the system component. Non-limiting examples of operations of the communication identifier circuit 310 include determining communicated information from the movement and/or vibration information of the system component, including determining that an event has occurred (e.g. a perforation gun has successfully fired), determining direct communications (e.g. logging or drilling data), determining that the system component is functioning correctly, and/or determining the position of a system component that is not visually observed (e.g. the current position downhole of a drill bit, perforation gun, etc.). A speaker and/or fluid reservoir may be observed for vibrations and/or movement information to provide a high signal observation surface for the EM interrogation device 104, and may include vibration and/or movement information from direct stimulus (e.g. fluid reservoir surface vibrating from proximity to a pump) and/or through analogized communication (e.g. vibration signal of a drill string converted to an electrical signal and communicated to a speaker in line of sight communication with the EM interrogation device 104). The described examples are non-limiting and provide a few example arrangements for purposes of illustration.

In certain aspects, the controller 112 further includes a perforation confirmation circuit 312, the perforation confirmation circuit 312 structured to determine at least one of a perforation indication 332 and a perforation location 334 in response to at least one value from the geologic movement identification circuit 302. An example perforation confirmation circuit 312 further interprets a highest amplitude position 354 of the movement profile 212 of the geological location 134, and determines the perforation location 334 in response to the highest amplitude position 354. The highest amplitude position 354 includes an amplitude such as a position displacement amplitude, a velocity amplitude, and/or an acceleration amplitude. An example perforation confirmation circuit 312 further interprets a temporal perforation value 336, and determines the at least one of the perforation indication 332 and the perforation location 334 further in response to the temporal perforation value 336.

An example controller 112 includes an energy communication circuit 308 vibrationally coupled to at least one system component such as a tubular extending from a well head, a well head, a treating line fluidly coupled to a well head, an earth based location, an artificial structure, a speaker, a fluid reservoir, and a plurality of distinct fluid reservoirs. An example perforation confirmation circuit 312 is further structured to determine the perforation indication 332 and/or the perforation location 334 in response to at least one communicated vibration 356 from the energy communication circuit 308. An example system 100 includes the energy communication circuit 308 including a perforating device.

In certain aspects, the controller 112 further includes a treatment integrity identification circuit 314 structured to determine a treatment integrity value 338 in response to the movement profile of the geological location 134. Example and non-limiting treatment integrity values 338 including a treatment success value, a treatment containment value, a treatment vertical extent value, a treatment horizontal extent value, and/or a treatment failure type value. A treatment integrity value 338 may be determined by observing motion, vibration, and/or detection of species of interest 252 found within an air volume, an observable fluid reservoir, and/or on a surface anywhere within the system 100. In certain embodiments, a diagnostic fluid reservoir in fluid communication with a formation of interest may be provided to allow for detection of a species of interest 252 (e.g. a species indicating fluid communication with a treatment operation) to assist in determining the treatment integrity value 338. Example and non-limiting diagnostic fluid reservoirs include a flowback pit from an offset well, and/or a flowback pit in fluid communication with a formation of interest (e.g. in an offset wellbore or from the same wellbore such as through an annulus of the wellbore).

In certain embodiments, a treatment success value can indicate that a treatment did not breach into a formation of interest near the treated formation (e.g. a water formation positioned vertically above the treated formation), that a treatment did not experience leaks or spills, that a treatment did not extend beyond a predetermined vertical extent, that a treatment did not extend beyond a predetermined horizontal extent, that a treatment did not communicate further into a formation than intended (e.g. to a formation in fluid communication with an offset wellbore), or any other value indicative of a treatment success or failure. One of skill in the art, having the benefit of the disclosures herein, can determine a treatment success value based upon information readily available about a contemplated system 100 and important to determining a treatment success for the system 100.

In certain embodiments, a treatment containment value can indicate that a treatment was contained within a predetermined vertical extent, that specified treating equipment did not leak or fail (e.g. treating lines, treating pumps, or a packer or other equipment within the wellbore), that a treatment was contained within a predetermined horizontal extent, and/or that a treatment was contained within scheduled geometric parameters (e.g. only the treating equipment, wellbore, formation, and/or flowback pit). One of skill in the art, having the benefit of the disclosures herein, can determine a treatment containment value based upon information readily available about a contemplated system 100 and important to determining treatment containment parameters for the system 100.

In certain embodiments, a treatment vertical extent value and/or a treatment horizontal extent value can be a value representative of a vertical and/or horizontal extent of a treatment operation. A value representative of the vertical and/or horizontal extent can be a value at which motion is observed, an observed height within a wellbore at which fluid communication with the treatment is observed (e.g. through communication in the same or an offset well at a plurality of vertical locations above a treatment entry point), an observed distance from a treatment entry point where horizontal fluid communication is observed (e.g. through communication with one or more of a plurality of offset wellbore or fluid communication points), or any other value which describes or can be analogized to a horizontal or vertical extent of a treatment. A treatment vertical extent and/or horizontal extent value may be representative of an actual extent of a treatment, an effective extent of a treatment (e.g. flow areas communicated to via the treatment), and/or may be quantitative (e.g. 100 feet horizontally) and/or categorical (e.g. communicated with formation "Beta" above the treatment formation, and/or communicated with flow points "1" through "3" above the formation or away from the treatment entry point). The described examples are non-limiting examples provided for illustration. One of skill in the art, having the benefit of the disclosures herein, can determine a treatment success value based upon information readily available about a contemplated system 100 and important to determining a treatment vertical extent and/or a treatment horizontal extent for the system 100.

In certain embodiments, a treatment failure type value can indicate that a treatment breached into a formation of interest near the treated formation (e.g. a water formation positioned vertically above the treated formation), that a treatment experienced leaks or spills, that a treatment extended beyond a predetermined vertical extent, that a treatment extended beyond a predetermined horizontal extent, that a treatment communicated further into a formation than intended (e.g. to a formation in fluid communication with an offset wellbore), that equipment failed during the treatment operation, or any other value indicative of a treatment failure. The treatment failure type value may include an indication of whether the treatment failed, and if the treatment failed, may further include an indication of the type of failure experienced. The treatment failure type value may be quantitative (e.g. extended 50 feet past the intended treatment depth, or extended 20 feet above an intended treatment height) and/or categorical (e.g. treatment failure status "FAILED," or treatment failure status "FAILED, LEAK ON TREATING JOINT 2"). Example and non-limiting treatment failure type values includes a value such as an equipment failure value, a pressure treatment height growth value, a treating line failure value, a well head failure value, and/or a wellbore failure value. One of skill in the art, having the benefit of the disclosures herein, can determine a treatment failure type value based upon information readily available about a contemplated system 100 and important to determining a treatment failure type for the system 100.

In certain aspects, the system 100 includes the EM interrogation device 104 further structured to interrogate at least one of an air volume in proximity to the geological location 134 and an investigation surface of the geographic location 134, wherein the EM radiation 210 includes at least a selected spectral frequency value 250, and wherein the EM interrogation device 104 is further structured to receive reflected EM radiation 210 including the spectral frequency value 250. The example system 100 further includes the controller 112 having a composition discrimination circuit 304 that determines, in response to the reflected EM radiation 210, the presence of a species of interest 252 in at least one of the air volume and on the investigation surface, and a treatment integrity identification circuit 314 that determines a treatment integrity value 338 in response to the presence of the species of interest 252. In certain further aspects, the treatment integrity value 338 includes at least one value such as a treatment success value, a treatment containment value, a treatment vertical extent value, a treatment horizontal extent value, and/or a treatment failure type value. An example system 100 further includes a diagnostic fluid reservoir in fluid communication with a second formation and optically visible to the EM interrogation device 104, where the treatment integrity identification circuit 314 is further structured to determine the treatment integrity value 338 in response to a presence of a species of interest 336 in the diagnostic fluid reservoir.

An example system 100 includes a second wellbore fluidly coupled to a second formation, a diagnostic fluid reservoir in fluid communication with the second formation and optically visible to the EM interrogation device 104, where the controller 112 further comprises a treatment integrity identification circuit 314 structured to determine a treatment integrity value 338 in response to a presence of a species of interest 336 in the diagnostic fluid reservoir. The example treatment integrity identification circuit 314 is further structured to receive treatment pressure information 340 (e.g. wirelessly through transceiver 128, or by any other method), and to determine that the treatment integrity value 314 is one of a wellbore failure value and a formation containment failure value further in response to the treatment pressure information 340. For example and without limitation, a pressure model of the reservoir may be performed during the treating operation and/or a predetermined modeled pressure trajectory may be available to the controller 112, and the pressure response evaluated in combination with the movement profile 212 and/or detection of a species of interest 252 to determine a treatment integrity value 314. Example species of interest 252 include at least one species such as $CO_2$, $H_2S$, a natural gas component, an acid, a tracer material, a tracer fluid substrate, a material indicative of a release of a treatment fluid, a material indicative of a release of formation gases, a material indicative of a release of wellhead gases, and/or a material indicative of a release of an energized treatment fluid.

An example system 100 includes a corner cube positioned at the geological location 134, with example corner cubes being one of a dihedral and a trihedral corner cube. The positioning of a corner cube can provide a high signal to noise ratio at the location of the corner cube, and can be utilized to improve both the signal response and/or the horizontal resolution of the movement profile 212 in the area of the corner cube(s). An example system 100 includes a number of corner cubes positioned at an area of high resolution interest within the geological location 134. Example and non-limiting areas of high resolution interest include at least one area such as an area proximate to a wellhead, an exploration area (e.g. for seismic determinations), a fracture description area, a communication area, and an area in vibrational communication with wellbore treating equipment.

An example system 100 includes a number of EM interrogation devices 104, 118 (but there may be more than two), where the movement profile 212 of the geological location 134 further includes at least one movement direction value (e.g. vertical, horizontal, or movement within a specified system of coordinates). An example controller 112 further including a wave identification circuit 316 structured to separate a compression wave value 342 and a shear wave value 344 in response to the movement profile 212 of the geological location 134. Example operations to separate a compression wave value 342 and a shear wave value 344 include at least deconvoluting movement from a compression wave and a shear wave through directional response indicated by the movement profile 212, and/or a timing of a movement response relative to an energy inducing event (e.g. recognizing that compression waves in most materials of interest propagate almost twice as fast as shear waves). It can be seen that one of skill in the art can prepare a system 100 to operate, in one example, as a seismometer over a large area at one time, within visual range of the EM interrogation device(s) 104, 118. Additionally or alternatively, the EM interrogation device(s) 104, 118 can cover large areas without clearing the land, for example using EM radiation (e.g., EM beam 108) frequencies, emitted by EM emitter 106 or other equivalent device that can penetrate foliage or other ground cover. This penetration to the ground can occur with a laser, or light based, EM system by light traveling between the leaves or other foliage. With low frequency EM radiation (e.g. EM radiation in the radio frequency band) the EM wave could travel through the leaves. Only a small portion of the light needs to hit the ground and return to obtain information from the ground. Accordingly, contrary to previously known systems, a system 100 of the disclosure can be used for geologic exploration, motion determination, and/or detection of the presence of species of interest without having to clear roads, disturb wildlife, and/or move equipment into the geological location 134. The use of multiple EM interrogation devices 104, 118, patterns in the seismic source impulse energy provision, and/or statistical deconvolution techniques can reduce the testing time required, and/or improve the accuracy of determinations about the seismology and geology in a given area.

An example system 100 includes a first EM interrogation device 104 having a first line of sight value to the geological location 134, a second EM interrogation device 118 having a second line of sight value to the geological location 134, and an azimuthal difference (e.g. relative to the horizontal at the location, relative to a plane parallel to sea level, and/or relative to another selected plane) between the first line of sight value and the second line of sight value. Example and non-limiting ranges for the azimuthal difference include between 15 degrees and 165 degrees, between 30 degrees and 150 degrees, between 45 degrees and 135 degrees, between 75 degrees and 105 degrees, and/or about 90 degrees.

In certain aspects, the system 100 further includes one or more EM interrogation devices 104, 118 further including an associated drift implementation circuit 318 to provide induced movement 346 of the associated EM interrogation device 104, 118 during the determining the movement profile 212, and/or between determinations of the movement profile 212. Example drift implementation circuit(s) 318 further induce at least one movement path such as a structured horizontal path, a structured vertical path, a structured path having horizontal and vertical components, a randomized horizontal path, a randomized vertical path, a structured path having randomized horizontal and randomized vertical components, a path having one of the horizontal and vertical components structured and the other of the horizontal and vertical components randomized, a path selected in response to a position value of a feature positioned at the geological location 134, a path selected in response to a change in a position value of a feature positioned at the geological location 134, and/or a path selected in response to a plurality of positions of interest at the geological location 134. Example and non-limiting operations of a drift implementation circuit 318 include randomized movement of an EM interrogation device 104, 118 that will reduce the impact of a structure at the geological location 134 that may block a line of sight view to an area of interest located within ground based area 102 of the geological location 134, determination that a structure has blocked a line of sight view to an area of interest 102 of the geological location 134 and movement of the EM interrogation device 104, 118 to establish a line of sight view to the area of interest 102, and/or structured movement (e.g. through a predetermined path or paths) of the EM interrogation device 104, 118 sufficient to provide at least periodic line of sight visibility to an area of interest 102 despite the presence of expected structures, and/or to provide at least periodic line of sight visibility to multiple areas of interest 102 of the geological location 134. In certain embodiments, a position value 348 of a structure (e.g. treating equipment, a frac tank, a drilling rig, a truck driving through the geological location 134) may be provided to the drift implementation circuit 318 (e.g. through communication, observation by the EM interrogation device 104, etc.), and the drift implementation circuit 318 constructs or adjusts the induced movement 346 in response to the position value 348 of the structure. While elements of the induced movement 346 from the drift implementation circuit 318 are described in terms of horizontal and vertical movement, it is understood that any coordinate system may be utilized, including but not limited to cylindrical coordinates (radial, angular, and height movement) and/or spherical coordinates (radial, phi, and theta movement). Additionally or alternatively, randomized movement should be interpreted broadly, and can include truly random movement, white noise movement, pseudo-random movement, structured movement based on a predetermined value set that simulates a randomized set, bounded random movement (e.g. with a minimum and/or maximum height, and/or with bounded horizontal ranges), movement allowing for and/or compensating for natural drift (e.g. from wind), or other randomized or pseudo-randomized values.

The term structured path, as used herein, should be understood broadly. A structured path is a path based at least partially on some predetermined elements, such as traversing through a scheduled path, traversing through a path utilized to provide line of sight to selected portions of the geological location 134 in some pattern, and/or traversing through a path selected to ensure that certain elements of the geological location 134 are observed periodically. A structured path may contain randomized elements (e.g. with perturbations or deviations added to a baseline scheduled traversal path) and/or may be changed or updated during the EM detection in response to changes at the geological location 134, and/or to determine whether changes at the geological location 134 have occurred.

In certain aspects, the system 100 includes the controller 112 further including a noise reducing circuit 320 structured to perform a noise reduction operation 238 on the reflected EM radiation 108, and where the geologic movement identification circuit 302 is further structured to determine the movement profile 212 of the geological location 134 in response to the noise reduction operationoperation 238. Example and non-limiting noise reduction operationoperation 238 operations include a common mode noise reduction, a band pass filter noise reduction, a gap band filter noise reduction, a low pass filter noise reduction, and/or a high pass filter noise reduction. An example noise reducing circuit 320 determines a noise frequency value 350, and performs the noise reduction operationoperation 238 to reduce noise in a signal of the reflected EM radiation 210 in response to the noise frequency value 350. An example noise reducing circuit 320 is further structured to determine the noise frequency value 350 as one of a communicated noise frequency value (e.g. operating equipment at the location transmitting engine and/or pump frequency values) and an observed noise frequency value (e.g. the EM interrogation device 104 determines that one or more movement values observed are likely to be noise related).

An example system 100 includes the controller 112 further including a treatment equipment description circuit 322 structured to determine a treatment equipment description value 358 in response to the reflected EM radiation 210. Example and non-limiting operations to determine the treatment equipment description value(s) 358 include taking vibrational information from observed surfaces of treating equipment, determining leak information from observed equipment, and/or taking vibrational information from observed surfaces in vibrational communication with the treating equipment). An example and non-limiting operation to determine a treatment equipment description value 358 includes determining whether a pump is operating properly or abnormally in response to vibrational information corresponding to the pump, such as the sequence and equality of vibration events. Additionally or alternatively, the treatment equipment description circuit 322 further determines the treatment equipment description value 358 via at least one operation such as directly observing movement of a mechanical portion of a target treatment equipment (e.g. observing the movement of pump plungers which may have a portion thereof in line of sight communication to the EM interrogation device 104), interrogating frequency based content from an observed surface, where the observed surface is in vibrational communication with a target treatment equipment, and/or and receiving synchronized communications 362 from at least one of a noise source and a target treatment equipment, and enhancing information from the reflected EM radiation 210 in response to the synchronized communications 362. The treatment equipment description circuit 322 can enhance vibrational observations with synchronized communications 362 (e.g. the state of each plunger and/or valve in the pump), or determine the operation of the pump through inferred information (e.g. determining whether the vibrational sequence observed is consistent with the overall pumping cycle), and may further combine other information, such as movement of a treating line relative to each plunger stroke. Accordingly, the treatment equipment description circuit 322 may determine one or more of whether a pump is operating normally, failing, has one or more plungers failed or failing, has one or more valves failing, and which plunger or valve is failing. While the operations of the treating equipment description circuit 322 have been described relative to a hydraulic positive displacement pump, the treating equipment description circuit 322 may be utilized relative to any equipment that can be diagnosed through vibrational, movement, and/or species release information, including but not limited to engines, mixers, centrifugal pumps, and/or valves.

An example controller 112 includes a treatment description integration circuit 324 that determines at least one treatment relevant parameter 360 in response to the treatment equipment description value 358, and provides the treatment relevant parameter 360 to a treatment controller (not shown). Example and non-limiting treatment relevant parameters 360 includes a fracture description value, a pump rate value, and/or a pump event value. For example, and without limitation, the treatment equipment description circuit 322 may provide an updated treatment rate (e.g. based on the failure, impending failure, or determined capability of a given pump or pumps, or the loss of a treatment line which could be closed off but potentially force the loss of a pump or pumps), and/or a change in a treatment plan (e.g. based upon equipment condition, a later needed pump rate will not be available, or equipment will not last for the time or load currently scheduled, or a proppant delivery rate requirement cannot be met for a current or subsequent stage of a treatment).

The schematic operational descriptions which follow provide illustrative embodiments of performing procedures for determining a movement profile 212 for a geological location, and/or for determining whether a species of interest 252 is present at a location of interest. Operations illustrated are understood to be exemplary only, and operations may be combined or divided, and added or removed, as well as re-ordered in whole or part, unless stated explicitly to the contrary herein. Certain operations illustrated may be implemented by a computer executing a computer program product on a non-transient computer readable storage medium, where the computer program product comprises instructions causing the computer to execute one or more of the operations, or to issue commands to other devices to execute one or more of the operations.

In certain aspects, a method that includes operations to interrogate a ground based area 102 with an EM beam 108, receiving reflected EM radiation 210 from the ground based area 102 of geological location 134, and determining a movement profile 212 of the ground based area 102 in response to the reflected EM radiation 210. Additionally or alternatively, the method includes operations to interrogate at least one of an air volume proximate to a ground based area 102 and a surface of interest proximate to a ground based area 102 with an EM beam 108, operations to receive reflected EM radiation 210 from the at least one of the air volume and the surface of interest, and operations to determine whether a species of interest 252 is present in the at least one of the air volume and on the surface of interest in response to the reflected EM radiation 210.

Example operations to interrogate an air volume include directing an EM beam 108 through the air volume, and determining an amount of absorption of EM radiation within a selected spectral frequency value 250 by the air volume. EM radiation 210 may be received as directly reflected off of molecules in the air volume, and/or may be reflected off of a surface having passed through the air volume. Where the EM beam 108 reflects off of a surface beyond the air volume, the received EM radiation 210 may have passed through the air volume twice, which can be accounted for in determining the amount of the species of interest 252 within the air volume. In certain embodiments, detection of the species of interest 252 is useful without determining how much of the species is present—for example when determining whether $H_2S$ is present on a location, determining whether a treating fluid has migrated to a location where it is expected or not expected, and/or determining whether a spill has occurred of a particular fluid. Additionally or alternatively, it may be useful to determine a concentration or other amount description of the species of interest 252, which is determinable by determining the amount of absorption, the line-of-sight distance through the air volume, the air pressure and/or temperature and/or other description of the overall amount of gas present in the air volume, a comparison to a normalized absorption level, the use of certain statistical techniques such as comparing the absorption of the species of interest to absorption observed by a background material present in a known or assumed concentration, and/or any other method understood in the art.

The selection of the spectral frequency 250 of interest includes determining which species are to be detected and the absorption spectrum of those species, determining the absorption spectrum of other background species known or expected to be present, accounting for cross-sensitivity from absorption by other species, accounting for convenient frequency values that can be provided by available EM sources, and/or accounting for the absorption spectrum of normalizing or comparison species. In certain embodiments, multiple frequency values, such as selected spectral frequency 250 and/or a range of frequency values will be included in the spectral frequency 250 of interest. In certain embodiments, a spectral frequency value 250 or values will be selected that have a lower indicia of absorption, in addition to or alternatively to values having a higher indicia of absorption, which can allow for continued resolution of detection in the presence of high concentrations of the species of interest 252 or in the presence of large air volumes where complete or near complete absorption may otherwise occur. In certain embodiments, an offset frequency from an absorption frequency may be selected—for example where a species of interest 252 still shows some absorption of the offset frequency even if it is a lower signal response than the absorption frequency.

Example and non-limiting species of interest 252 include $CO_2$, $H_2S$, a natural gas component, a hydrocarbon fluid, a tracer material, a tracer material substrate, an acid, a material indicative of a release of a treatment fluid, a material indicative of a release of formation gases, a material indicative of a release of wellhead gases, a material indicative of a release of an energized treatment fluid, a material indicating a potential hazard, and a material indicating a potential environmental issue. Example and non-limiting tracer materials include radioactive, chemical, or dye-based tracers. In certain embodiments, the EM detection method can determine the presence of a tracer material or tracer material substrate (e.g. the fluid in which a tracer material is placed, which could be different from a treatment material fluid in an EM-detectable manner) before and/or at lower concentrations than can be detected by other methods such as a visual inspection (e.g. of flowback fluids, spilled fluids, or the like).

In certain embodiments, a method includes EM interrogation with an EM beam 108 of a ground based area 102, such as a tubular extending from a well head, a well head, a treating line fluidly coupled to a well head, treating equipment positioned at the geological location, an earth based location, an artificial structure, a pump, a fluid pit, and/or a fluid positioned in the fluid pit. EM interrogation can include determining at least any one of the presence of a species of interest 252 on or in proximity to the ground based area 102, determining a movement profile 212 of the ground based area 102 (such as displacement, velocity, and/or acceleration), determining frequency content of the ground based area 102 (such as frequency of vibration, phase of vibration, frequency amplitudes at one or more frequency values, etc.), and/or determining the geometry of the ground based area 102 (e.g. volume or change in volume of an amount of fluid).

An example method includes an operation to determine at least one of a volume of fluid in a fluid reservoir 326 and a differential volume of fluid in a fluid reservoir 328. Example fluid reservoirs include a drilling mud pit, a fluid flowback pit, and/or a treatment fluid supply reservoir. In certain embodiments, EM detection can determine information about a fluid reservoir more accurately and/or more rapidly than other methods—for example determining that a loss of circulation is occurring in response to the amount of fluid returning. Presently available methods such as utilizing flow meters are prone to high error values, and excessive integrating error over time. Additionally or alternatively, EM detection can determine the composition of flowback fluids and/or circulating fluids more rapidly and precisely than alternative methods.

An example method includes operations to determine vibrational information from at least one component, such as a tubular extending from a well head, a well head, a treating line fluidly coupled to a well head, an earth based location, an artificial structure, a speaker, and/or a fluid reservoir, all of which may be considered a ground based area 102 or part of a ground based area 102. An example operation includes providing a speaker in line of sight visibility to the EM interrogation device 104, where the EM interrogation device 104 can take information in real time from vibrational analysis of the speaker. The speaker can be configured to respond to analog information to be transmitted, such as electrical pulses generated from any sensor or device on a location, respond to movement in a manner that generates a stronger signal than direct observation by the EM interrogation device 104 and/or that would not be visible to the EM interrogation device 104 (e.g. a piezoelectric sensor determining deflection or movement somewhere within the wellbore, etc.), and/or the speaker can be configured to provide communication of any selected information directly to the EM interrogation device 104—such as logging information, pumping information, the status of any equipment on location, real-time modeling parameters from a treatment model, etc. The use of a speaker provides great flexibility in transferring information to the EM interrogation device 104 and additionally allows for synchronization of information where the determination of movement or detection of a species, or the information derived therefrom, can be enhanced by providing real-time synchronized information to the EM interrogation device 104. In certain embodiments, equipment (e.g. pump) vibration or other vibration information is communicated to the speaker in real-time, and can be used to diagnose the equipment and/or in signal processing to deconvolute noise vibration from signal vibration.

An example method includes operations to provide vibrational information with an energy communication circuit 308, the energy communication circuit 308 including at least one device such as a logging device, an explosive device, a physical impulse device, a measurement while drilling (MWD) device, a logging while drilling (LWD) device, and/or a physical stimulus device. Any energy source or communication mechanism for an energy source is contemplated herein. The example method includes an operation to interpret a communication 356 from the energy communication circuit 308 in response to the movement profile 212 of the ground based area 102 or a larger portion of a geological location 134, which includes a velocity value 220, a position value 222, 348, an acceleration value 224, a frequency value 226, a phase value 228, and/or a time value 230. The energy communication circuit 308 includes providing the communicated information 356 in a manner visible to the EM interrogation device 104, which includes without limitation providing a physical impulse that moves (e.g. by being in vibrational contact with the original energy provider or through one or more devices vibrationally coupled to the energy provider) any object in line of sight to the EM interrogation device 104, adjusting a speed of a rotating drill string (which is detectable by the EM interrogation device 104), and/or by providing electrical impulses to a speaker which provides analogous movement information for the EM interrogation device 104. In certain embodiments, the energy communication circuit 308 includes an amount of fluid (e.g. a puddle or a fluid reservoir) present in line of sight communication to the EM interrogation device 104, where the amount of fluid is in vibrational communication with the energy source. In certain embodiments, the surface of the amount of fluid may be more vibrationally sensitive and/or provide a stronger detectable movement signal than an amount of earth or artificial structure similarly positioned relative to the energy source.

An example method includes an operation to determine at least one of a perforation indication 332 and a perforation location 334 in response to at least one value from the movement profile 212 of the geological location. Example and non-limiting operations to determine the perforation indication 332 and/or location 334 include an operation to interpret a highest amplitude position 354 of the geologic movement profile 212, and an operation to determine the perforation location 334 in response to the highest amplitude position 354 (e.g. determining that a corresponding surface location is positioned at the highest amplitude position 354, and determining a corresponding sub-surface location). Examples of highest amplitude positions 354 include at least one amplitude, such as a position displacement amplitude, a velocity amplitude, and an acceleration amplitude. In certain embodiments, a corresponding surface location may be determined to be in a position where a greatest amplitude in observed in a frequency domain analysis, and in a further example may be determined to be a highest amplitude position 354 observed for selected frequency peaks (e.g. frequencies determined empirically, through analysis of the type of explosive and formation properties, resonant frequencies of wellbore equipment in communication with the perforating explosive, etc.).

In certain embodiments, a method includes an operation to interpret a temporal perforation value 336 (e.g. via a signal contemporaneous with a perforating gun command from a controller associated with the perforating operation), and determining the at least one of the perforation indication 332 and the perforation location 334 further in response to the temporal perforation value 336. In certain embodiments, signals provided during the perforating event can be processed differently, and/or expected areas relevant to the perforating determination can be processed with higher resolution and/or detection speed during the perforating operation. An example method includes a pressure sensor responsive to the perforating event, and communicatively coupled to the EM interrogation device 104 (e.g. through a speaker or wireless communications). An example method includes providing vibration information 330 with an energy communication circuit 308, interpreting the vibration information 330 from the energy communication circuit 308, and determining the at least one of the perforation indication 332 and the perforation location 334 further in response to the vibration information 330, where the energy communication circuit 308 includes a tubular extending from a well head, a well head, a treating line fluidly coupled to a well head, an earth based location, an artificial structure, a speaker, a fluid reservoir, and a plurality of distinct fluid reservoirs, and/or where the energy communication circuit 308 includes a perforating device.

An example method includes an operation to determine a treatment integrity value 338 in response to the reflected EM radiation 210. Example and non-limiting treatment integrity values 338 include a treatment success value, a treatment containment value, a treatment vertical extent value, a treatment horizontal extent value, and a treatment failure type value. Example and non-limiting treatment failure type values include a value such as an equipment failure value, a pressure treatment height growth value, a treating line failure value, a well head failure value, and a wellbore failure value. In certain embodiments, the method includes an operation to determine a treatment integrity value 338 in response to the presence of the species of interest 252.

In certain embodiments, the method includes an operation to interrogate a ground based area 102 comprising a diagnostic reservoir in fluid communication with a second wellbore fluid coupled to a second formation, and an operation to determine the treatment integrity value 338 further in response to the presence of a species of interest 252 in the diagnostic fluid reservoir. An example diagnostic fluid reservoir includes a fluid reservoir having an amount of fluid from a second formation that is not the treated formation—such as a formation above or near the treated formation—where the presence of a treatment related fluid or species indicative of breakthrough of a treatment related fluid into the second formation indicates that a treatment has not been contained, and/or that a treatment should be adjusted or discontinued.

In certain embodiments, breakthrough into another formation may be by design or according to design (e.g. substrate fluid only may be an indication of successful bridging by a fluid loss material or proppant). In certain embodiments, it may be desirable for a treatment to extend into the second formation, and presence of a species of interest 252 may indicate treatment success. In certain embodiments, the verification that a species of interest 252 is not present in the second formation may be an indication of treatment success, and can provide verification that the treatment was successful. In certain embodiments, the ground based area 102 comprising a diagnostic fluid reservoir may be fluidly coupled to the second formation within the same wellbore where the treatment is being performed (e.g. through an annulus of a tubular), and/or the diagnostic fluid reservoir may be fluidly coupled to the second formation from an offset wellbore. In certain embodiments, the diagnostic fluid may be coupled to the same formation as the treating formation, for example to determine that a treatment has not extended horizontally past a planned distance, and/or to determine certain parameters about the formation (e.g. such as the fracture gradient direction)—for example a plurality of offset wells may be fluidly coupled to the formation and diagnostic reservoirs, and the amount and/or presence of a species of interest 252 may be used to identify properties of the treated formation. The use of an EM interrogation device 104 or a small number of EM interrogation devices 104 118 allows for real-time determination of species of interest 252 in a number of geographically distributed locations simultaneously within the ground based area 102 or larger area 134, with greater detection capability than other methods, and without having to provide numerous sensors and communications thereto.

An example method includes an operation to receive treatment pressure information 340, and determining the treatment integrity value 338 further in response to the treatment pressure information 340. For example, the treatment pressure information 340 may be communicated in real-time to the EM interrogation device 104, and information from the treatment pressure information 340 may be combined with any or all of the information provided by the EM interrogation device (e.g. the movement profile 212 and/or detection of species of interest 252) to verify and/or adjust a model of the treatment either in real time or after the treatment is completed. Additionally or alternatively, treatment parameters such as fluid viscosity, breaker scheduling, fluid loss additives, and/or pump rates, may be modified either in real time or on subsequent treatments for the same or similar formations.

In one example, the EM interrogation device 104 may determine that greater height growth is occurring than an originally calibrated model indicates, and model parameters are adjusted to account for the observed height growth. A treatment may then be adjusted, in real time or for a subsequent treatment, to utilize a lower viscosity fluid, to add bridging materials to avoid growth into an offset formation, pump rates may be lowered, total pump volumes may be lowered, changing a fluid type for compatibility purposes, and/or any other changes may be made to the treatment in response.

In another example, the EM interrogation device 104 may determine that greater horizontal extension is occurring than an originally calibrated model indicates, and model parameters are adjusted to account for the observed horizontal extent of the treatment. A treatment may then be adjusted, in real time or for a subsequent treatment, such as increasing a viscosity of the treating fluid, reducing fluid loss additives, and/or reducing a pumping rate (e.g. to induce a tip screen out of the fracture).

In certain aspects, the method includes positioning a corner cube at the geological location. The presence of a corner cube can enhance the signal-to-noise experienced at the corner cube location, and enhance the horizontal area resolution of received signals for the EM interrogation device 104 in the region of the corner cube. An example method includes positioning a number of corner cubes at an area of high resolution interest within the geological location. Example and non-limiting areas of high resolution interest include an area proximate to a wellhead, an exploration area, a fracture description area (e.g. an area above where a fracture is expected to occur, or where it should be verified that a fracture has not occurred), a communication area (e.g. an area where movement information is being provided to communicate with the EM interrogation device), and an area in vibrational communication with wellbore treating equipment. Example corner cubes may be bihedral (two interior sides) and/or trihedral (three interior sides).

An example method includes performing the interrogating with a plurality of EM beams 108, 122 from a plurality of EM interrogation devices 104, 118, and separating a compression wave value 342 and a shear wave value 344 in response to reflected EM radiation 210 from the plurality of EM beams. In the example, movement direction can be determined from multiple EM interrogation devices 104, 118, determining which aspects of the movement are attributable to a compression wave 342 and which aspects are attributable to a shear wave 344 passing through the ground based area 102. In certain embodiments, distinguishing a compression wave from a shear wave can be performed utilizing a single EM interrogation device 104—for example with reliance on the speed differences of propagation of compression and shear waves from the wave inducing source (e.g. a seismic hammer or explosive). In certain embodiments, a method includes performing the interrogating with a first EM interrogation device 104 having a first line of sight value and with a second EM interrogation device 118 having a second line of sight value, with the first line of sight value and second line of sight values having an azimuthal difference there between. The azimuthal difference values between the first line of sight value and the second line of sight value may be any difference value between 0 degrees and 180 degrees, including without limitation values in the range of between 15 degrees and 165 degrees, between 30 degrees and 150 degrees, between 45 degrees and 135 degrees, between 75 degrees and 105 degrees, and about 90 degrees.

In certain embodiments, more than two EM interrogation devices (not shown) are provided, with at least two of the EM interrogation devices having an azimuthal difference in the line of sight between the EM interrogation devices. Example and non-limiting orientations for three EM interrogation devices include: the devices could equally distributed around the ground based area 102 or larger geological location 134 (120 degree spacing); a first device 104 at zero degrees and a second device 118 at 90 degrees, with the third device (not shown) at any other location (e.g. 225 degrees for equal spacing relative to each of the first two devices, at zero or 90 degrees for redundancy with one of the first two devices, at 180 or 270 degrees to provide a second 90 degree spacing option between two of the devices, or any other value). The selection of the number of EM interrogation devices and the azimuthal spacing there between is a mechanical step for one of skill in the art having the benefit of the disclosure herein.

An example method includes an operation to induce movement of an EM interrogation device 104 performing the interrogating. Example operations to induce movement of the EM interrogation device include utilizing at least one movement path such as a structured horizontal path, a structured vertical path, a structured path having horizontal and vertical components, a randomized horizontal path, a randomized vertical path, a structured path having randomized horizontal and randomized vertical components, a path having one of the horizontal and vertical components structured and the other of the horizontal and vertical components randomized, a path selected in response to a position value of a feature positioned at the geological location, a path selected in response to a change in a position value of a feature positioned at the geological location, and a path selected in response to a plurality of positions of interest at the geological location.

An example method includes performing a noise reduction operation 238 on the reflected EM radiation 210, where performing the noise reduction operation 238 includes a common mode noise reduction, a band pass filter noise reduction, a gap band filter noise reduction, a low pass filter noise reduction, and/or a high pass filter noise reduction. The frequency bands selected for the band pass, gap band, low pass, and/or high pass filter noise reductions may be selected to isolate a known, expected, or observed noise at the location—such as noise from treating equipment vibration and/or noise sources known or suspected to exist in the geological area. An example method further includes determining a noise frequency value 350, and performing the noise reduction operation 238 in response to the noise frequency value 350. Determining the noise frequency value 350 may be based on known, expected, and/or observed noise.

An example method includes an operation to determine a treatment equipment description value 358 in response to the reflected EM radiation 210. Example operations to determine the treatment equipment description value 358 include performing at least one operation such as directly observing movement of a mechanical portion of a target treatment equipment, interrogating frequency based content from an observed surface, where the observed surface is in vibrational communication with a target treatment equipment, and/or receiving synchronized communications from at least one of a noise source and a target treatment equipment, and enhancing information from the reflected EM radiation 210 in response to the synchronized communications. An example method includes an operation to determine at least one treatment relevant parameter 360 in response to the treatment equipment description value 358, and to provide the treatment relevant parameter 360 to a treatment controller. Example and non-limiting treatment relevant parameters 360 includes at least one value such as a fracture description value, a pump rate value, and/or a pump event value. Example fracture description values include a fracture vertical extent, a fracture horizontal extent, and/or a treatment integrity value according to any description of a treatment integrity value described herein.

An aspect of the present disclosure includes a method including directing an electromagnetic (EM) beam 108 at a ground based area 102, receiving reflected EM radiation 210 from the EM beam 108 at a detector array 110, and determining a movement profile 212 of the ground based area 102. Certain further aspects of the present disclosure include determining the movement profile 212 of the ground based area 102 to include determining a description of ground based movement corresponding to at least a portion of the ground based area 102, the description of the ground based movement including a velocity value 220, a position value 222, 348, an acceleration value 224, a frequency value 226, a phase value 228, and/or a time value 230; further synchronizing the determining the movement profile 212 of the ground based area 102 to an external event 234, and relating at least a portion of the movement profile 212 to the external event 234 in the time domain; inducing a ground energy event 240, and wherein the determining the movement profile 212 of the ground based area 102 is in response to the inducing; determining the movement profile 212 of the ground based area 102 to include determining at least one arrival time event 242; determining the movement profile 212 of the ground based area 102 to further include determining a position 244 of the inducing of a ground energy event; determining the movement profile 212 of the ground based area 102 to further include determining an extent 246 of the inducing of a ground energy event 240 and/or a containment of the inducing of the ground energy event; determining the movement profile 212 of the ground based area 102 with a spatial resolution value 214 that is not greater than 1 square foot pixels, not greater than 1 square inch pixels, and/or not greater than 1 square centimeter pixels; determining a plurality of movement profiles 212 from a plurality of detector arrays 110 124 positioned around the ground based area 102; determining the movement profile 212 of the ground based area 102 to further include performing a common mode noise reduction operation 218; interpreting a time synchronized known noise value 236, and wherein the determining the movement profile 212 further includes performing a known noise reduction operation 238 in response to the time synchronized known noise value 236; interrogating an air volume in proximity to the ground based area 102 with EM radiation including at least a selected spectral frequency value 250, receiving reflected EM radiation 210 from the EM radiation including the selected spectral frequency value 250, and determining the presence of a species of interest 252 in the air volume in response to the reflected EM radiation 210, and/or wherein the species of interest 252 may further include $CO_2$, $H_2S$, a natural gas component, and/or a tracer material; wherein the movement profile further comprises a depth of field value of not greater than 1 mm; and/or the ground based area including an earth based structure and/or an artificial structure.

Another aspect of the present disclosure includes a system having a ground based area 102, an electromagnetic (EM) interrogation device 104 having an EM emitter 106 structured to direct an EM beam 108 at the ground based area 102, and having a detector array 110 structured to receive reflected EM radiation 210 from the EM beam 108, and a controller 112 having a ground movement description module 202 structured to determine a movement profile 212 of the ground based area 102 in response to the reflected EM radiation 210. Certain further aspects of the present disclosure include the ground movement description module 202 further structured to determine the movement profile 212 in response to a velocity value 220, a position value 222, 348, an acceleration value 224, a frequency value 226, a phase value 228, and/or a time value 230; the controller 112 further including a synchronization module 204 structured to interpret a time profile value 232 corresponding to an external event 234, and to synchronize the determining of the movement profile 212 to the external event 234, and wherein the ground movement description module 202 is further structured to relate at least a portion of the movement profile 212 to the external event 234 in the time domain; an energy inducing device 114a operationally coupled to the ground based area 102 and wherein the ground movement description module 202 is further structured to determine the movement profile 212 further in response to an energy inducing event 240 from the energy inducing device 114a, and/or where ground movement description module 202 is further structured to determine the movement profile 212 further in response to an energy inducing event 240 by determining at least one arrival time event 242 of the energy inducing event, and/or where the ground movement description module 202 is further structured to determine the movement profile 212 further in response to an energy inducing event 240 by determining a position 244 of the energy inducing event, and/or where the energy inducing device 114a comprises an explosive device, a hydraulic hammer, a sonic device, an ultrasonic device, an electrically operated device, a pneumatically operated device, a hydraulic inducement, and/or a hydraulically operated device, and/or where the ground movement description module 202 is further structured to determine the movement profile 212 further in response to an energy inducing event 240 by determining an extent 246 of the inducing, and/or where the ground movement description module 202 is further structured to determine a containment 248 of the inducing in response to the movement profile 212; where the movement profile comprises a spatial resolution value 214 that is not greater than 1 square foot pixels, not greater than 1 square inch pixels, and/or not greater than 1 square centimeter pixels.

The system further including a plurality of EM interrogation devices 104, 118 corresponding to a plurality of EM emitters 106, 120, each structured to direct a corresponding EM beam 108, 122 at the ground based area 102, and each having a corresponding detector array structured to receive reflected EM radiation 210 from the corresponding EM beams 108, 122; and at least one controller 112 having at least one ground movement description module 202 structured to determine a plurality of movement profiles 212 of the ground based area 102 in response to the reflected EM radiation 210 from each of the corresponding EM beams 108, 122. The ground movement description module 202 is further structured to determine the movement profile 212 in response to a common mode noise reduction operation 218; where the controller 112 further includes a noise input module 206 structured to interpret a time synchronized known noise value 236, and wherein the ground movement description module 202 is further structured to determine the movement profile 212 in response to a known noise reduction operation 238 performed in response to the time synchronized known noise value 236. The system further includes a gas composition detector (not shown—but it can share the same equipment with the EM emitter 106) structured to interrogate an air volume in proximity to the ground based area with an EM radiation including at least a selected spectral frequency value 250, a second detector array 124 structured to receive the reflected EM radiation 210 having the selected spectral frequency value 250 and to provide a detected response value 254, and wherein the controller 112 further comprises a composition determination module 208 structured to determine a gas composition value 256 in response to the detected response value 254, and/or where the gas composition value 256 includes the indication of a species of interest 252 in the air volume in proximity to the ground based area 102, and/or where the species of interest 252 includes $CO_2$, $H_2S$, a natural gas component, and/or a tracer material. The movement profile 212 further comprises a depth of field value 216 of not greater than 1 mm; and/or where the ground based area 102 includes an earth based structure and/or an artificial structure.

Yet another aspect of the present disclosure is a method for determining movement of a ground-based area 102, including illuminating the ground-based area 102 with an electro-magnetic (EM) radiation device, such as EM emitter 106, receiving reflected EM radiation 210 from the ground-based area 102 in response to the illuminating, processing the reflected EM radiation 210 to determine movement profile 212 of at least a portion of the ground-based area in response to the receiving the reflected EM radiation 210, and in response to the determining the movement information, performing at least one response operation, the response operation including diagnosing a ground based operation in response to the movement information, diagnosing a ground based device in response to the movement information, receiving a communication from a device in vibrational communication with the ground-based area in response to the movement area, and/or determining a status of a ground based operation in response to the movement information.

Certain further aspects of the present disclosure include illuminating the ground-based area 102 with an electro-magnetic (EM) radiation device, such as EM emitter 106 further includes operating a differential absorption EM detection and receiving device, operating a Laser Induced Breakdown Spectroscopy (LIBS) device, and/or operating a Laser Induced Fluorescence (LIF) device, where the method further includes identifying a species of interest 252 in the air volume in proximity to the ground-based area 102; and/or where determining the movement profile 212 information further includes determining a displacement value, also known as a position value 222, a velocity value 220, an acceleration value 224, a vibration value, and/or determining movement frequency information of at least a portion of the ground-based area.

Certain further aspects of the present disclosure are set forth herein. An aspect of the present disclosure includes a system having a ground based area 102 within a larger geological location 134, an electromagnetic (EM) interrogation device 104 having an EM emitter 106 structured to direct an EM beam 108 at the ground based area 102 of larger geological location 134, and having a detector array 110 structured to receive reflected EM radiation 210 from the EM beam 108, and a controller 112 having a geologic movement identification circuit 302 structured to determine a movement profile 212 of the ground based area 102 of the larger geological location 134 in response to the reflected EM radiation 210.

Certain aspects of the present disclosure further include the geological location comprising a ground based area 102, having at least one of an oilfield location, a gas well location, an oil well location, a disposal well location, a water well location, a coal bed methane well location, a shale oil location, a location including a horizontal well, a location including a well fluidly coupled to a hydrocarbon formation having sour hydrocarbons, a location including a well fluidly coupled to a shallow formation, and/or a location including an exploration area. Certain aspects of the system include the EM interrogation device 104 being further structured to interrogate an air volume in proximity to the ground based area 102 with EM radiation (e.g., EM beam 108) including at least a selected spectral frequency value 250 and to receive reflected EM radiation 210 including the selected spectral frequency value 250, and wherein the controller 112 further comprises a composition discrimination circuit 304 structured to determine the presence of a species of interest 252 in the air volume in response to the reflected EM radiation 210. In certain embodiments, the EM interrogation device 104 is further structured to interrogate the air volume receiving reflected EM radiation 210 from gas molecules present in the air volume, and/or receiving reflected EM radiation 210 that has passed through the air volume. In certain embodiments, the species of interest 252 includes $CO_2$, $H_2S$, a natural gas component, a tracer material, a material indicative of a release of a treatment fluid, a material indicative of a release of formation gases, a material indicative of a release of wellhead gases, and/or a material indicative of a release of an energized treatment fluid.

In certain aspects, the system includes the geological location being an investigation surface, where the EM interrogation device 104 is further structured to interrogate the investigation surface with EM radiation including at least a selected spectral frequency value 250 and to receive reflected EM radiation 210 including the selected spectral frequency value 250, and the controller 112 further including a composition discrimination circuit 304 that determines the presence of a species of interest 252 on the investigation surface in response to the reflected EM radiation 210. Example and non-limiting species of interest 252 include a treatment fluid, a wellbore fluid, a treatment constituent, an acid, a tracer material, a tracer fluid substrate, and/or a hydrocarbon fluid.

In certain aspects, the ground based area 102 includes a tubular extending from a well head, a well head, a treating line fluidly coupled to a well head, treating equipment positioned at the geological location, an earth based location, an artificial structure, a pump, a fluid pit, and a fluid positioned in a fluid pit; the controller further including a fluid reservoir volume resolving circuit structured to determine a volume of fluid in a fluid reservoir and/or a differential volume of fluid in a fluid reservoir, and/or the fluid reservoir being a drilling mud pit, a fluid flowback pit, and/or a treatment fluid supply reservoir.

In certain aspects, the system includes an energy communication circuit 308 vibrationally coupled to at least one system component such as a tubular extending from a well head, a well head, a treating line fluidly coupled to a well head, an earth based location, an artificial structure, a speaker, and/or a fluid reservoir; where the energy communication circuit includes at least one of a logging device, an explosive device, a physical impulse device, a measurement while drilling (MWD) device, a logging while drilling (LWD) device, and/or a physical stimulus device; and/or the controller 112 further including a communication identifier circuit 310 that interprets a communication from the energy communication circuit 308 in response to at least one value from the geologic movement identification circuit 302, the at least one value corresponding to the system component, and the at least one value including at least one of a velocity value 220, a position value 222, 348, an acceleration value 224, a frequency value 226, a phase value 228, and/or a time value 230.

In certain aspects, the controller 112 further includes a perforation confirmation circuit 312, the perforation confirmation circuit 312 structured to determine at least one of a perforation indication 332 and a perforation location 334 in response to at least one value from the geologic movement identification circuit 302; the perforation confirmation circuit 312 further structured to interpret a highest amplitude position 354 of the movement profile 212 of the geological location, and to determine the perforation location 334 in response to the highest amplitude position 354; where the highest amplitude position 354 includes an amplitude such as a position displacement amplitude, a velocity amplitude, and/or an acceleration amplitude; the perforation confirmation circuit 312 further structured to interpret a temporal perforation value 336, and to determine the at least one of the perforation indication 332 and the perforation location 334 further in response to the temporal perforation value 336; an energy communication circuit 308 vibrationally coupled to at least one system component such as a tubular extending from a well head, a well head, a treating line fluidly coupled to a well head, an earth based location, an artificial structure, a speaker, a fluid reservoir, and a plurality of distinct fluid reservoirs, and where the perforation confirmation circuit 308 is further structured to determine the perforation indication 332 and/or the perforation location 334 in response to at least one communicated vibration 356 from the energy communication circuit 308; and/or the energy communication circuit 308 including a perforating device.

In certain aspects, the controller 112 further includes a treatment integrity identification circuit 314 structured to determine a treatment integrity value 338 in response to the movement profile 212 of the geological location; the treatment integrity value 338 including at least one value such as a treatment success value, a treatment containment value, a treatment vertical extent value, a treatment horizontal extent value, and/or a treatment failure type value; and/or the treatment failure type value includes a value such as an equipment failure value, a pressure treatment height growth value, a treating line failure value, a well head failure value, and a wellbore failure value. Values such as treatment success value, a treatment containment value, a treatment vertical extent value, a treatment horizontal extent value, and/or a treatment failure type value and/or the treatment failure type value includes a value such as an equipment failure value, a pressure treatment height growth value, a treating line failure value, a well head failure value, and a wellbore failure value are all non-limiting examples of treatment relevant parameters 360.

In certain aspects, the system includes the EM interrogation device 104 further structured to interrogate at least one of an air volume in proximity to the ground based area 102 and an investigation surface located within the ground based area 102, wherein the EM radiation, such as EM beam 108, includes at least a selected spectral frequency value 250, and wherein the EM interrogation device 104 is further structured to receive reflected EM radiation 210 including the selected spectral frequency value 250, and the controller 112 further includes a composition discrimination module 208 that determines, in response to the reflected EM radiation 210, the presence of a species of interest 252 in at least one of the air volume and on the investigation surface located within ground based area 102, and a treatment integrity identification circuit 314 that determines a treatment integrity value 338 in response to the presence of the species of interest 252. In certain further aspects, the treatment integrity value 338 includes at least one value such as a treatment success value, a treatment containment value, a treatment vertical extent value, a treatment horizontal extent value, and/or a treatment failure type value; the treatment failure type value includes a value such as an equipment failure value, a treating line failure value, a formation containment failure value, a well head failure value, and/or a wellbore failure value; the system further including a diagnostic fluid reservoir in fluid communication with a second formation and optically visible to the EM interrogation device 104, where the treatment integrity identification circuit 314 is further structured to determine the treatment integrity value 338 in response to a presence of a species of interest 252 in the diagnostic fluid reservoir.

In certain aspects, the system includes a second wellbore fluidly coupled to a second formation, a diagnostic fluid reservoir in fluid communication with the second formation and optically visible to the EM interrogation device 104, where the controller 112 further comprises a treatment integrity identification circuit 314 structured to determine a treatment integrity value 338 in response to a presence of a species of interest 252 in the diagnostic fluid reservoir; the treatment integrity identification circuit 314 is further structured to receive treatment pressure information 340, and to determine that the treatment integrity value 338 is one of a wellbore failure value and a formation containment failure value further in response to the treatment pressure information 340; where the species of interest 252 includes at least one species such as $CO_2$, $H_2S$, a natural gas component, an acid, a tracer material, a tracer fluid substrate, a material indicative of a release of a treatment fluid, a material indicative of a release of formation gases, a material indicative of a release of wellhead gases, and/or a material indicative of a release of an energized treatment fluid.

In certain aspects, the system includes a corner cube positioned at the geological location; the corner cube being one of a dihedral and a trihedral corner cube; a number of corner cubes positioned at an area of high resolution interest within the geological location; and/or the area of high resolution interest including at least one area such as an area proximate to a wellhead, an exploration area, a fracture description area, a communication area, and an area in vibrational communication with wellbore treating equipment.

In certain aspects, the system includes a number of EM interrogation devices 104, 118, where the movement profile 212 of the ground based area 102 of a geological location further includes at least one movement direction value; the controller 112 further including a wave identification circuit 316 structured to separate a compression wave value 342 and a shear wave value 344 in response to the movement profile 212 of the geological location; a first EM interrogation device 104 includes a first line of sight value to the geological location, a second EM interrogation device 118 includes a second line of sight value to the geological location, and an azimuthal difference between the first line of sight value and the second line of sight value including at least one of difference values such as between 15 degrees and 165 degrees, between 30 degrees and 150 degrees, between 45 degrees and 135 degrees, between 75 degrees and 105 degrees, and/or about 90 degrees.

In certain aspects, the system further includes each EM interrogation device 104, 118 further including an associated drift implementation circuit 318 structured to induce movement of the associated EM interrogation device 104, 118 during the determining the movement profile 212; each drift implementation circuit 318 further structured to induce at least one movement path such as a structured horizontal path, a structured vertical path, a structured path having horizontal and vertical components, a randomized horizontal path, a randomized vertical path, a structured path having randomized horizontal and randomized vertical components, a path having one of the horizontal and vertical components structured and the other of the horizontal and vertical components randomized, a path selected in response to a position value of a feature positioned at the geological location, a path selected in response to a change in a position value 222, 348 of a feature positioned at the geological location, and/or a path selected in response to a plurality of positions of interest at the geological location.

In certain aspects, the system includes the controller 112 further including a noise reducing circuit 320 structured to perform a noise reduction operation 238 on the reflected EM radiation 210, and where the geologic movement identification circuit 302 is further structured to determine the movement profile 212 of the geological location in response to the noise reduction operation 238; where the noise reduction operation 238 includes at least one noise reduction operation such as a common mode noise reduction operation 218, a band pass filter noise reduction, a gap band filter noise reduction, a low pass filter noise reduction, and/or a high pass filter noise reduction; the noise reducing circuit 320 is further structured to determine a noise frequency value 350, and to perform the noise reduction operation 238 to reduce noise in a signal of the reflected EM radiation 210 in response to the noise frequency value 350; and/or the noise reducing circuit 320 is further structured to determine the noise frequency value 350 as one of a communicated noise frequency value and an observed noise frequency value.

In certain aspects, the system includes the controller 112 further including a treatment equipment description circuit 322 structured to determine a treatment equipment description value 358 in response to the reflected EM radiation 210; where the treatment equipment description circuit 322 is further structured to determine the treatment equipment description value 358 via at least one operation such as directly observing movement of a mechanical portion of a target treatment equipment, interrogating frequency based content from an observed surface, where the observed surface is in vibrational communication with a target treatment equipment, and/or and receiving synchronized communications from at least one of a noise source and a target treatment equipment, and enhancing information from the reflected EM radiation 210 in response to the synchronized communications; where the controller 112 further includes a treatment description integration circuit 324 structured to determine at least one treatment relevant parameter 360 in response to the treatment equipment description value 358, and to provide the treatment relevant parameter 360 to a treatment controller; and/or where the treatment relevant parameter 360 includes at least one value such as a fracture description value, a pump rate value, and a pump event value.

In certain aspects, the disclosure includes a method including interrogating a geological location with an EM beam 108, receiving reflected EM radiation 210 from the geological location, and determining a movement profile 212 of the geological location in response to the reflected EM radiation 210.

In certain aspects, the disclosure includes a method including interrogating at least one of an air volume proximate to a geological location and a surface of interest proximate to a geological location with an EM beam 108, receiving reflected EM radiation 210 from the at least one of the air volume and the surface of interest, and determining whether a species of interest 252 is present in the at least one of the air volume and on the surface of interest in response to the reflected EM radiation 210.

In certain further aspects, the method includes receiving reflected EM radiation 210 from the air volume by at least one operation such as receiving reflected EM radiation 210 from gas molecules present in the air volume, and receiving reflected EM radiation that has passed through the air volume; where the species of interest 252 includes at least one species such as $CO_2$, $H_2S$, a natural gas component, a hydrocarbon fluid, a tracer material, a tracer material substrate, an acid, a material indicative of a release of a treatment fluid, a material indicative of a release of formation gases, a material indicative of a release of wellhead gases, a material indicative of a release of an energized treatment fluid, a material indicating a potential hazard, and a material indicating a potential environmental issue; where the interrogating further includes interrogating with EM radiation including a selected spectral frequency value 250; where the geological location includes at least one member such as a tubular extending from a well head, a well head, a treating line fluidly coupled to a well head, treating equipment positioned at the geological location, an earth based location, an artificial structure, a pump, a fluid pit, and a fluid positioned in the fluid pit; determining at least one of a volume of fluid 326 in a fluid reservoir and a differential volume of fluid 328 in a fluid reservoir; and/or where the fluid reservoir includes at least one of a drilling mud pit, a fluid flowback pit, and a treatment fluid supply reservoir.

In certain aspects, the method includes determining vibration information 330 from a ground based area 102 comprising at least one component such as a tubular extending from a well head, a well head, a treating line fluidly coupled to a well head, an earth based location, an artificial structure, a speaker, and the fluid reservoir. The method includes providing vibration information 330 with an energy communication circuit 308, the energy communication circuit 308 including at least one energy inducing device 114*a* such as a logging device, an explosive device, a physical impulse device, a measurement while drilling (MWD) device, a logging while drilling (LWD) device, and a physical stimulus device. The method further includes interpreting a communication from the energy communication circuit 308 in response to at least one value from the movement profile 212 of the ground based area 102 of larger geological location 134, wherein the at least one value from the movement profile 212 of the ground based area 102 of larger geological location includes at least one parameter such as a velocity value 220, a position value 222, 348, an acceleration value 224, a frequency value 226, a phase value 228, and a time value 230. Next, the method includes determining at least one of a perforation indication 332 and a perforation location 334 in response to at least one value from the movement profile 212 of the ground based area 102; determining the at least one of the perforation indication 332 and the perforation location 334 by interpreting a highest amplitude position 354 of the geologic movement profile and determining the perforation location 334 in response to the highest amplitude position 354; where the highest amplitude position 354 includes at least one amplitude such as a position displacement amplitude, a velocity amplitude, and an acceleration amplitude; interpreting a temporal perforation value 336, and determining the at least one of the perforation indication 332 and the perforation location 334 further in response to the temporal perforation value 336. Next, the method includes providing vibration information 330 with an energy communication circuit 308, interpreting the vibration 330 information from the energy communication circuit 308, and determining the at least one of the perforation indication 332 and the perforation location 334 further in response to the vibration 330 information; where the energy communication circuit 308 includes at least one component such as a tubular extending from a well head, a well head, a treating line fluidly coupled to a well head, an earth based location, an artificial structure, a speaker, a fluid reservoir, and a plurality of distinct fluid reservoirs; and/or where the energy communication circuit 308 includes a perforating device.

In certain aspects, the method includes determining a treatment integrity value 338 in response to the reflected EM radiation 210; determining the treatment integrity value 338 as at least one value such as a treatment success value, a treatment containment value, a treatment vertical extent value, a treatment horizontal extent value, and a treatment failure type value; the treatment failure type value including a value such as an equipment failure value, a pressure treatment height growth value, a treating line failure value, a well head failure value, and a wellbore failure value; determining a treatment integrity value 338 in response to the presence of the species of interest 252; where the treatment integrity value 338 includes at least one value such as a treatment success value, a treatment containment value, a treatment vertical extent value, a treatment horizontal extent value, and a treatment failure type value; the treatment failure type value including a value such as an equipment failure value, a pressure treatment height growth value, a treating line failure value, a well head failure value, and a wellbore failure value; interrogating a diagnostic reservoir in fluid communication with a second wellbore fluid coupled to a second formation, and where the determining the treatment integrity value 338 is further in response to the presence of the species of interest 252 in the diagnostic fluid reservoir; and/or receiving treatment pressure information, and where the determining the treatment integrity value 338 is further in response to the treatment pressure information 340.

In certain aspects, the method includes positioning a corner cube at the geological location; positioning a number of corner cubes at an area of high resolution interest within the geological location; where the area of high resolution interest includes at least one area such as an area proximate to a wellhead, an exploration area, a fracture description area, a communication area, and an area in vibrational communication with wellbore treating equipment; performing the interrogating with a plurality of EM beams 108, 122 from a plurality of EM interrogation devices 104,118; separating a compression wave value 342 and a shear wave value 344 in response to reflected EM radiation 210 from the plurality of EM beams 108, 122; and/or performing the interrogating with a first EM interrogation device 104 having a first line of sight value and with a second EM interrogation device 118 having a second line of sight value, and providing an azimuthal difference between the first line of sight value and the second line of sight value, where the azimuthal difference comprises at least one difference value such as between 15 degrees and 165 degrees, between 30 degrees and 150 degrees, between 45 degrees and 135 degrees, between 75 degrees and 105 degrees, and about 90 degrees.

In certain aspects, the method includes inducing movement of an EM interrogation device 104 performing the interrogating; and/or inducing movement of the EM interrogation device utilizing at least one movement path such as a structured horizontal path, a structured vertical path, a structured path having horizontal and vertical components, a randomized horizontal path, a randomized vertical path, a structured path having randomized horizontal and randomized vertical components, a path having one of the horizontal and vertical components structured and the other of the horizontal and vertical components randomized, a path selected in response to a position value of a feature positioned at the geological location, a path selected in response to a change in a position value of a feature positioned at the geological location, and a path selected in response to a plurality of positions of interest at the geological location.

In certain aspects, the method includes performing a noise reduction operation 238 on the reflected EM radiation 210; performing the noise reduction operation 238 by performing at least one operation such as a common mode noise reduction 218, a band pass filter noise reduction, a gap band filter noise reduction, a low pass filter noise reduction, and a high pass filter noise reduction; determining a noise frequency value, and performing the noise reduction operation 238 in response to the noise frequency value 350; determining a treatment equipment description value 358 in response to the reflected EM radiation 210; where the determining the treatment equipment description value 358 further includes performing at least one operation such as directly observing movement of a mechanical portion of a target treatment equipment, interrogating frequency based content from an observed surface, wherein the observed surface is in vibrational communication with a target treatment equipment, and receiving synchronized communications from at least one of a noise source and a target treatment equipment, and enhancing information from the reflected EM radiation 210 in response to the synchronized communications; determining at least one treatment relevant parameter 360 in response to the treatment equipment description value 358, and providing the treatment relevant parameter 360 to a treatment controller (not shown), which could be part of controller 112; and/or where the treatment relevant parameter 360 includes at least one value such as a fracture description value, a pump rate value, and/or a pump event value.

As is evident from the figures and text presented above, a variety of embodiments according to the present disclosure are contemplated. Any example system and/or module described herein may include any known hardware and/or process to implement the described features. One of skill in the art, having the benefit of the disclosures herein, will understand various embodiments to implement aspects of the disclosures herein. In certain embodiments, certain features may be implemented in accordance with certain hardware and/or processes described in the "Field Guide to Lidar," by Paul McManamon, published by SPIE Press as ISBN-13:978-16284 16541, and ISBN-10:16284 16548, available as of Mar. 30, 2015 on www.amazon.com, which is incorporated herein by reference in the entirety for all purposes.

While the invention has been illustrated and described in detail in the drawings and foregoing description, the same is to be considered as illustrative and not restrictive in character, it being understood that only certain exemplary embodiments have been shown and described. Those skilled in the art will appreciate that many modifications are possible in the example embodiments without materially departing from this invention. Accordingly, all such modifications are intended to be included within the scope of this disclosure as defined in the following claims.

In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A system for improving oil field operations, comprising:
an electromagnetic (EM) interrogation device having an EM emitter structured to direct an EM beam at an aboveground geological location, the EM interrogation device including a spatial heterodyne EM detector array structured to receive from the aboveground geological location a reflected EM radiation from the EM beam; and a controller having a geologic movement identification circuit structured to determine a surface movement profile of the aboveground geological location in response to the reflected EM radiation.

2. The system of claim 1, wherein the aboveground geological location comprises at least one location selected from a group comprising a ground based area, an oilfield location, a gas well location, an oil well location, a disposal well location, a water well location, a coal bed methane well location, a shale oil location, a location including a horizontal well, a location including a well fluidly coupled to a hydrocarbon formation having sour hydrocarbons, a location including a well fluidly coupled to a shallow formation, a tubular extending from a well head, a well head, a treating line fluidly coupled to a well head, treating equipment positioned at the geological location, an earth based location, an artificial structure, a pump, a fluid pit, and a fluid positioned in a fluid pit, and a location including an exploration area.

3. The system of claim 2, wherein the controller further comprises a fluid reservoir volume resolving circuit structured to determine at least one of a volume of fluid in a fluid reservoir and a differential volume of fluid in a fluid reservoir.

4. The system of claim 3, further comprising an energy communication circuit vibrationally coupled to at least one of the locations of the group of aboveground geological locations.

5. The system of claim 4, wherein the energy communication circuit comprises at least one device selected from a group of devices comprising a logging device, an explosive device, a physical impulse device, a measurement while drilling (MWD) device, a logging while drilling (LWD) device, and a physical stimulus device.

6. The system of claim 5, wherein the controller further comprises a communication identifier circuit structured to interpret a communication from the energy communication circuit in response to at least one value from the geologic movement identification circuit, the at least one value corresponding to the at least one of the locations of the group of aboveground geological locations, and the at least one value including at least one parameter selected from the parameters comprising a velocity value, a position value, an acceleration value, a frequency value, a phase value, and a time value.

7. The system of claim 2, wherein the controller further comprises a perforation confirmation circuit, the perforation confirmation circuit structured to determine at least one of a perforation indication and a perforation location in response to at least one value from the geologic movement identification circuit, the perforation confirmation circuit further structured to interpret a highest amplitude position of the surface movement profile of the aboveground geological location, and to determine the perforation location in response to the highest amplitude position, the highest amplitude position including at least one amplitude selected from a group comprising a position displacement amplitude, a velocity amplitude, and an acceleration amplitude.

8. The system of claim 7, wherein the perforation confirmation circuit is further structured to interpret a temporal perforation value and to determine the at least one of the perforation indication and the perforation location further in response to the temporal perforation value.

9. The system of claim 7, further comprising an energy communication circuit vibrationally coupled to at least one of the locations of the group of aboveground locations wherein the perforation confirmation circuit is further structured to determine the at least one of the perforation indication and the perforation location in response to at least one communicated vibration from the energy communication circuit.

10. The system of claim 2, wherein the controller further comprises a treatment integrity identification circuit structured to determine a treatment integrity value in response to the surface movement profile of the aboveground geological location.

11. The system of claim 10, wherein the treatment integrity value includes at least one value selected from a group comprising a treatment success value, a treatment containment value, a treatment vertical extent value, a treatment horizontal extent value, and a treatment failure type value.

12. The system of claim 10, further comprising a diagnostic fluid reservoir in fluid communication with a second aboveground geological location and optically visible to the EM interrogation device, wherein the treatment integrity identification circuit is further structured to determine the treatment integrity value in response to a presence of a species of interest in the diagnostic fluid reservoir.

13. The system of claim 12, wherein the species of interest comprises at least one species selected from a group comprising $CO_2$, $H_2S$, a natural gas component, an acid, a tracer material, a tracer fluid substrate, a material indicative of a release of a treatment fluid, a material indicative of a release of formation gases, a material indicative of a release of wellhead gases, and a material indicative of a release of an energized treatment fluid.

14. The system of claim 10, wherein the treatment integrity identification circuit is further structured to receive a treatment pressure information and to determine that the treatment integrity value is one of a wellbore failure value and a formation containment failure value further in response to the treatment pressure information.

15. The system of claim 1, wherein the EM interrogation device is further structured to interrogate an air volume in proximity to the aboveground geological location with EM radiation including at least a selected spectral frequency value and to receive reflected EM radiation including the spectral frequency value, and wherein the controller further comprises a composition discrimination circuit structured to determine the presence of a species of interest in the air volume in response to the reflected EM radiation.

16. The system of claim 15, wherein the interrogation device is further structured to interrogate the air volume by at least one operation selected from a group comprising receiving reflected EM radiation from gas molecules present in the air volume, and receiving reflected EM radiation that has passed through the air volume.

17. The system of claim 1, wherein the EM interrogation device includes a first EM interrogation device having a first line of sight value to the aboveground geological location and a second EM interrogation device having a second line of sight value to the aboveground geological location, wherein an azimuthal difference between the first line of sight value and the second line of sight value includes at least one of the difference values comprising between 15 degrees and 165 degrees, between 30 degrees and 150 degrees, between 45 degrees and 135 degrees, between 75 degrees and 105 degrees, and about 90 degrees.

18. The system of claim 17, wherein each EM interrogation device further includes an associated drift implementation circuit structured to induce movement of the associated EM interrogation device when determining the surface movement profile, each drift implementation circuit further structured to induce at least one movement path selected from a group comprising a structured horizontal path, a structured vertical path, a structured path having horizontal and vertical components, a randomized horizontal path, a randomized vertical path, a structured path having randomized horizontal and randomized vertical components, a path having one of the horizontal and vertical components structured and the other of the horizontal and vertical components randomized, a path selected in response to a position value of a feature positioned at the aboveground geological location, a path selected in response to a change in a position value of a feature positioned at the aboveground geological location, and a path selected in response to a plurality of positions of interest at the aboveground geological location.

19. The system of any one of claim 17, wherein the species of interest comprises at least one species selected from the group comprising $CO_2$, $H_2S$, a natural gas component, a tracer material, a material indicative of a release of a treatment fluid, a material indicative of a release of formation gases, a material indicative of a release of wellhead gases, and a material indicative of a release of an energized treatment fluid.

20. The system of claim 1 wherein the controller further comprises at least one of a wave identification circuit structured to separate a compression wave value and a shear wave value in response to the movement profile of the aboveground geological location, a noise reducing circuit structured to perform a noise reduction operation on the reflected EM radiation, and a treatment equipment description circuit structured to determine a treatment equipment description value in response to the reflected EM radiation, and a treatment description integration circuit structured to determine at least one treatment relevant parameter in response to the treatment equipment description value, and to provide the treatment relevant parameter to a treatment controller.

21. The system of claim 1, wherein the aboveground geological location includes an investigation surface, wherein the EM interrogation device is further structured to interrogate the investigation surface with EM radiation including at least a selected spectral frequency value and to receive reflected EM radiation including the spectral frequency value, and the controller further comprises a composition discrimination circuit structured to determine the presence of a species of interest on the investigation surface in response to the reflected EM radiation.

22. A system for improving oil field operations, comprising:
an electromagnetic (EM) interrogation device having an EM emitter structured to direct an EM beam at an aboveground geological location, the aboveground geological location including at least one location selected from a group comprising a ground based area, an oilfield location, a gas well location, an oil well location, a disposal well location, a water well location, a coal bed methane well location, a shale oil location, a location including a horizontal well, a location including a well fluidly coupled to a hydrocarbon formation having sour hydrocarbons, a location including a well fluidly coupled to a shallow formation, a tubular extending from a well head, a well head, a treating line fluidly coupled to a well head, treating equipment positioned at the aboveground geological location, an earth based location, an artificial structure, a pump, a fluid pit, a fluid positioned in a fluid pit, and a location including an exploration area;
the EM interrogation device further including a spatial heterodyne EM detector array structured to receive from the aboveground geological location reflected EM radiation, the reflected EM radiation including at least a spectral frequency value, the EM interrogation device structured to interrogate the aboveground geological location and an investigation surface of the aboveground geographic location;
a controller having at least one of a geologic movement identification circuit structured to determine a surface movement profile of the aboveground geological location in response to the reflected EM radiation, a composition discrimination circuit structured to determine, in response to the reflected EM radiation, the presence of a species of interest in at least one of the air volume and on the investigation surface, and a treatment integrity identification circuit structured to determine a treatment integrity value in response to the presence of the species of interest.

23. The system of claim 22, wherein the treatment integrity value comprises at least one value selected from a group comprising a treatment success value, a treatment containment value, a treatment vertical extent value, a treatment horizontal extent value, and a treatment failure type value, the treatment failure type value including a value selected from a group comprising an equipment failure value, a treating line failure value, a formation containment failure value, a well head failure value, and a wellbore failure value.

24. The system of claim 23, further comprising a wellbore fluidly coupled to a second aboveground geological location, a diagnostic fluid reservoir in fluid communication with the second aboveground geological location and optically visible to the EM interrogation device, wherein the controller further comprises a treatment integrity identification circuit structured to determine a treatment integrity value in response to the species of interest in the diagnostic fluid reservoir.

25. A method, comprising:
interrogating at least one of an aboveground geological location and a surface of interest proximate to the aboveground geological location with an EM beam;
receiving using a spatial heterodyne EM detector array reflected EM radiation from the at least one of the aboveground geological location and the surface of interest proximate to the aboveground geological location; and
determining at least one of a surface movement profile of the aboveground geological location in response to the reflected EM radiation and whether a species of interest is present on the surface of interest in response to the reflected EM radiation.

26. The method of claim 25, further comprising determining vibrational information from at least one component selected from a tubular extending from a well head, a well head, a treating line fluidly coupled to a well head, an earth based location, an artificial structure, a speaker, and the fluid reservoir.

27. The method of claim 26, further comprising providing vibrational information with an energy communication circuit, the energy communication circuit including at least one device selected from a group comprising a logging device, an explosive device, a physical impulse device, a measurement while drilling (MWD) device, a logging while drilling (LWD) device, and a physical stimulus device.

28. The method of claim 27, further comprising interpreting a communication from the energy communication circuit in response to at least one value from the surface movement profile of the aboveground geological location, wherein the at least one value from the movement profile of the aboveground geological location comprises at least one parameter selected from a group comprising a velocity value, a position value, an acceleration value, a frequency value, a phase value, and a time value.

29. The method of claim 25, further comprising determining at least one of a perforation indication and a perforation location in response to at least one value from the surface movement profile of the aboveground geological location.

30. The method of claim 29, wherein the determining the at least one of the perforation indication and the perforation location includes interpreting a highest amplitude position of the surface movement profile and determining the perforation location in response to the highest amplitude position, wherein the highest amplitude position consists of at least one amplitude selected from a position displacement amplitude, a velocity amplitude, and an acceleration amplitude.

31. The method of claim 30, further comprising providing vibrational information with an energy communication circuit, interpreting the vibrational information from the energy communication circuit, and determining the at least one of the perforation indication and the perforation location further in response to the vibrational information.

32. The method of claim 25, further comprising determining a treatment integrity value in response to the reflected EM radiation, the treatment integrity value including at least one value selected from a group comprising a treatment success value, a treatment containment value, a treatment vertical extent value, a treatment horizontal extent value, and a treatment failure type value, the treatment failure type value includes a value selected from a group comprising an equipment failure value, a pressure treatment height growth value, a treating line failure value, a well head failure value, and a wellbore failure value.

33. The method of claim 25, further comprising determining a treatment integrity value in response to the presence of the species of interest, the treatment integrity value comprising at least one value selected from a group comprising a treatment success value, a treatment containment value, a treatment vertical extent value, a treatment horizontal extent value, and a treatment failure type value, the treatment failure type value includes a value selected from a group comprising an equipment failure value, a pressure treatment height growth value, a treating line failure value, a well head failure value, and a wellbore failure value.

34. The method of claim 25, further comprising performing the interrogating with a plurality of EM beams from a plurality of EM interrogation devices.

35. The method of claim 34, further comprising separating a compression wave value and a shear wave value in response to reflected radiation from the plurality of EM beams.

36. The method of claim 34, wherein the plurality of EM interrogation devices includes a first EM interrogation device having a first line of sight value and with a second EM interrogation device having a second line of sight value, and providing an azimuthal difference between the first line of sight value and the second line of sight value, wherein the azimuthal difference comprises at least one difference value selected from the difference values consisting of: between 15 degrees and 165 degrees, between 30 degrees and 150 degrees, between 45 degrees and 135 degrees, between 75 degrees and 105 degrees, and about 90 degrees.

37. The method of claim 36, further comprising inducing movement of at least one of the plurality of the EM interrogation devices.

38. The method of claim 37, wherein the inducing movement of the at least one of the EM interrogation devices comprises inducing at least one movement path selected from a group comprising a structured horizontal path, a structured vertical path, a structured path having horizontal and vertical components, a randomized horizontal path, a randomized vertical path, a structured path having randomized horizontal and randomized vertical components, a path having one of the horizontal and vertical components structured and the other of the horizontal and vertical components randomized, a path selected in response to a position value of a feature positioned at the aboveground geological location, a path selected in response to a change in a position value of a feature positioned at the aboveground geological location, and a path selected in response to a plurality of positions of interest at the aboveground geological location.

39. The method of claim 25, further comprising performing a noise reduction operation on the reflected EM radiation, the noise reduction operation including performing at least one operation selected from a group comprising a common mode noise reduction, a band pass filter noise reduction, a gap band filter noise reduction, a low pass filter noise reduction, and a high pass filter noise reduction.

40. The method of claim 25 further comprising determining a treatment equipment description value in response to the reflected EM radiation, wherein the determining the treatment equipment description value includes performing at least one operation selected from a group comprising directly observing movement of a mechanical portion of a target treatment equipment, interrogating frequency based content from an observed surface, wherein the observed surface is in vibrational communication with a target treatment equipment, receiving synchronized communications from at least one of a noise source and a target treatment equipment, and enhancing information from the reflected EM radiation in response to the synchronized communications.

* * * * *